US012806057B2

(12) United States Patent
Murdock et al.

(10) Patent No.: US 12,806,057 B2
(45) Date of Patent: Nov. 24, 2026

(54) EXTERNAL SPINAL BRACE

(71) Applicant: THINKS WORKS, PBC, Austin, TX (US)

(72) Inventors: Ryan C. Murdock, Austin, TX (US); Robert James Jones, Lago Vista, TX (US)

(73) Assignee: THINKS WORKS, PBC, Austin, TX (US)

( * ) Notice: Subject to any disclaimer, the term of this patent is extended or adjusted under 35 U.S.C. 154(b) by 4 days.

(21) Appl. No.: 18/872,889

(22) PCT Filed: Jul. 16, 2023

(86) PCT No.: PCT/US2023/070297
§ 371 (c)(1),
(2) Date: Dec. 9, 2024

(87) PCT Pub. No.: WO2024/020330
PCT Pub. Date: Jan. 25, 2024

(65) Prior Publication Data

US 2026/0076815 A1 Mar. 19, 2026

Related U.S. Application Data

(60) Provisional application No. 63/420,962, filed on Oct. 31, 2022, provisional application No. 63/390,076, filed on Jul. 18, 2022.

(51) Int. Cl.
*A61F 5/02* (2006.01)

(52) U.S. Cl.
CPC .............. *A61F 5/026* (2013.01); *A61F 5/028* (2013.01)

(58) Field of Classification Search
CPC .......... A61F 5/024; A61F 5/026; A61F 5/028; A41D 13/0531; A61B 17/60; A61B 17/64;
(Continued)

(56) References Cited

U.S. PATENT DOCUMENTS 2,835,247 A 5/1958 Stabholc
3,889,664 A 6/1975 Heuser et al.
(Continued)

FOREIGN PATENT DOCUMENTS

CA 3049756 A1 7/2017
CN 2264574 Y 10/1997
(Continued)

OTHER PUBLICATIONS

European Patent Office, Extended European Search Report dated Oct. 6, 2025 in European Patent Application No. 23843780.0 (12 pages).

(Continued)

*Primary Examiner* — Keri J Nelson
*Assistant Examiner* — Seth R. Brown
(74) *Attorney, Agent, or Firm* — Trop, Pruner & Hu, P.C.

(57) ABSTRACT

A spinal support system that includes interchangeable bushings (having different degrees of tilt) and a curved sacral segment that has variable settings. The bushings and sacral segment collectively produce variable levels of spinal distraction and may be combined in different ways to generally apply different forces, as selected by a user, onto the spine of a patient.

28 Claims, 52 Drawing Sheets

(58) Field of Classification Search
CPC ............ A61B 17/6425; A61B 17/6433; A61B 17/645
USPC .......................................................... 602/19
See application file for complete search history.

(56) References Cited

U.S. PATENT DOCUMENTS

| | | | | |
|---|---|---|---|---|
| 3,926,182 | A | 12/1975 | Stabholz | |
| 5,449,338 | A | 9/1995 | Trudell | |
| 5,876,361 | A | 3/1999 | Harris | |
| 6,687,920 | B2 | 2/2004 | Berns | |
| 6,964,644 | B1 | 11/2005 | Garth | |
| 7,654,973 | B2 | 2/2010 | Firsov | |
| 7,662,121 | B2 | 2/2010 | Zours | |
| 7,988,652 | B2 | 8/2011 | Chao | |
| 9,216,121 | B2 | 12/2015 | Galante | |
| 9,504,307 | B1 | 11/2016 | Burnett et al. | |
| 10,206,805 | B2 | 2/2019 | Murdock | |
| 11,123,214 | B2 | 9/2021 | Wilson et al. | |
| 11,166,834 | B2 | 11/2021 | Murdock | |
| 11,877,945 | B2 | 1/2024 | Murdock | |
| 2008/0234691 | A1 * | 9/2008 | Schwab | A61B 17/7013 606/100 |
| 2010/0268137 | A1 | 10/2010 | Bachmann et al. | |
| 2014/0224849 | A1 * | 8/2014 | Hiemenz | A41D 13/0531 224/271 |
| 2015/0141891 | A1 | 5/2015 | Wang | |
| 2015/0272808 | A1 | 10/2015 | Lee | |
| 2017/0196722 | A1 * | 7/2017 | Murdock | A61F 5/028 |
| 2019/0076287 | A1 * | 3/2019 | Wilson | A61F 5/028 |
| 2020/0000621 | A1 | 1/2020 | Saban | |
| 2020/0229760 | A1 | 7/2020 | DeLuke et al. | |
| 2024/0156630 | A1 | 5/2024 | Murdock | |

FOREIGN PATENT DOCUMENTS

| | | | |
|---|---|---|---|
| CN | 2676868 | Y | 2/2005 |
| CN | 2787173 | Y | 6/2006 |
| CN | 200939192 | Y | 8/2007 |
| CN | 110974515 | B | 8/2020 |
| CN | 213372770 | U | 6/2021 |
| DE | 19543566 | A1 | 5/1997 |
| DE | 102011076843 | B4 | 5/2014 |
| EP | 1685814 | A1 | 2/2006 |
| EP | 3426200 | B1 | 1/2020 |
| EP | 3402356 | B1 | 8/2023 |
| KR | 20160091025 | A | 8/2016 |
| WO | 2009038493 | A1 | 3/2009 |
| WO | 2017123466 | A1 | 7/2017 |
| WO | 2020156617 | A1 | 8/2020 |
| WO | 2020234244 | A2 | 11/2020 |
| WO | 2024020330 | A1 | 1/2024 |

OTHER PUBLICATIONS

International Search Authority, International Search Report and Written Opinion dated Oct. 31, 2023 in International Application No. PCT/US2023/070297 (9 pages).

"Jewett® J-35 Hyperextension Brace", downloaded from https://www.pelsupply.com/product/910 on Mar. 10, 2021 (two pages).

Yilmaz, "Bracing In Adolescent Idiopathic Scoliosis", The Journal of Turkish Spinal Surgery, vol. 27, Issue: 4, Jul. 2016. pp. 253-266.

Bushing (isolator), Wikipedia, retrieved from https://en.wikipedia.org/w/index.php?title=Bushing_(isolator)&oldid=1083677985, Apr. 20, 2022 (two pages).

Fuss et al., "Pressure Sensor System for Customized Scoliosis Braces", Sensors 2021, 21, 1153 (19 pages).

* cited by examiner

SECTION B-B

SECTION A-A

SECTION B-B

SECTION A-A

SECTION A-A

SECTION B-B

SECTION A-A

SECTION B-B

SECTION B-B

SECTION A-A

SECTION B-B

SECTION A-A

SECTION B-B

SECTION A-A

SECTION A-A

SECTION B-B

EXTERNAL SPINAL BRACE

CROSS-REFERENCE TO RELATED APPLICATION

This application is a § 371 national stage of International Application No. PCT/US23/70297, filed Jul. 16, 2023 and entitled "External Spinal Brace", which claims priority to both: (a) U.S. Provisional Patent Application No. 63/390,076 filed on Jul. 18, 2022 and entitled "External Spinal Brace"; and (b) U.S. Provisional Patent Application No. 63/420,962 filed on Oct. 31, 2022 and entitled "External Spinal Brace". The content of each of the above applications is hereby incorporated by reference.

TECHNICAL FIELD

Embodiments of the invention are in the field of external spinal braces that apply distraction, bending, and/or torsional forces to a patient's spine.

BACKGROUND

As provided in U.S. Pat. No. 10,206,805, Scoliosis is a medical condition in which a person's spinal axis has a three-dimensional deviation. Other disorders associated with abnormalities in spinal alignment include, for example, Scheuermann's kyphosis, congenital scoliosis, neuromuscular conditions, paralysis, dystonia, and injuries of the spine. Such disorders may have far-flung consequences for the entire musculoskeletal system and in some instances can lead to organ dysfunction. Effective treatment and rehabilitation of such problems require complex therapies that take into account and have an effect on the entire musculoskeletal system.

Several surgical and nonsurgical methods have been tried in an attempt to treat such disorders of the spine. Surgical methods which have been used are in general highly invasive and involve, for example, coupling multiple metal rods to a subject's spine using multiple screws. Such highly invasive surgical procedures typically require a long and arduous recuperation period.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
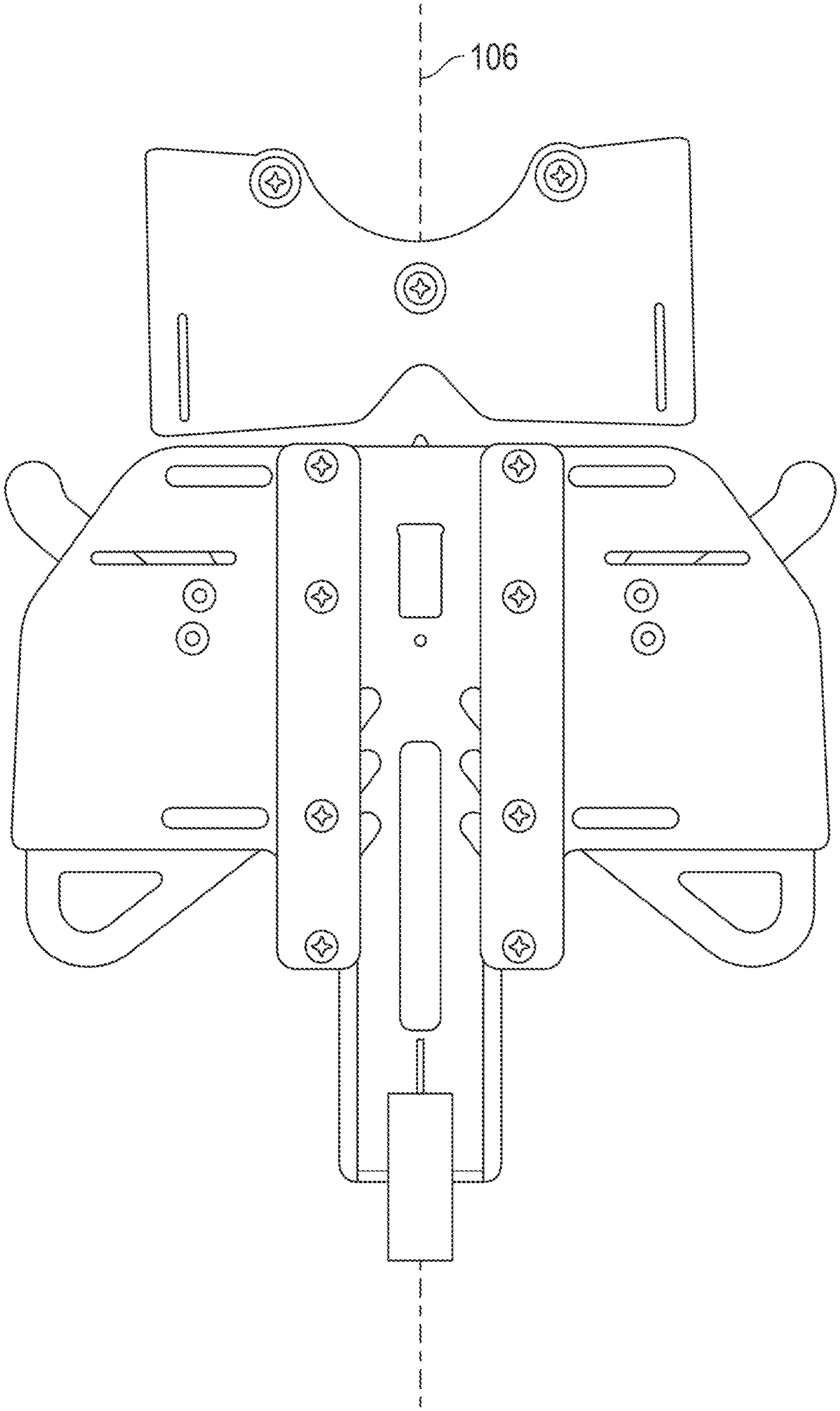
FIG. 1 includes an embodiment of a ratchet system.
Figures 2A, 2B:
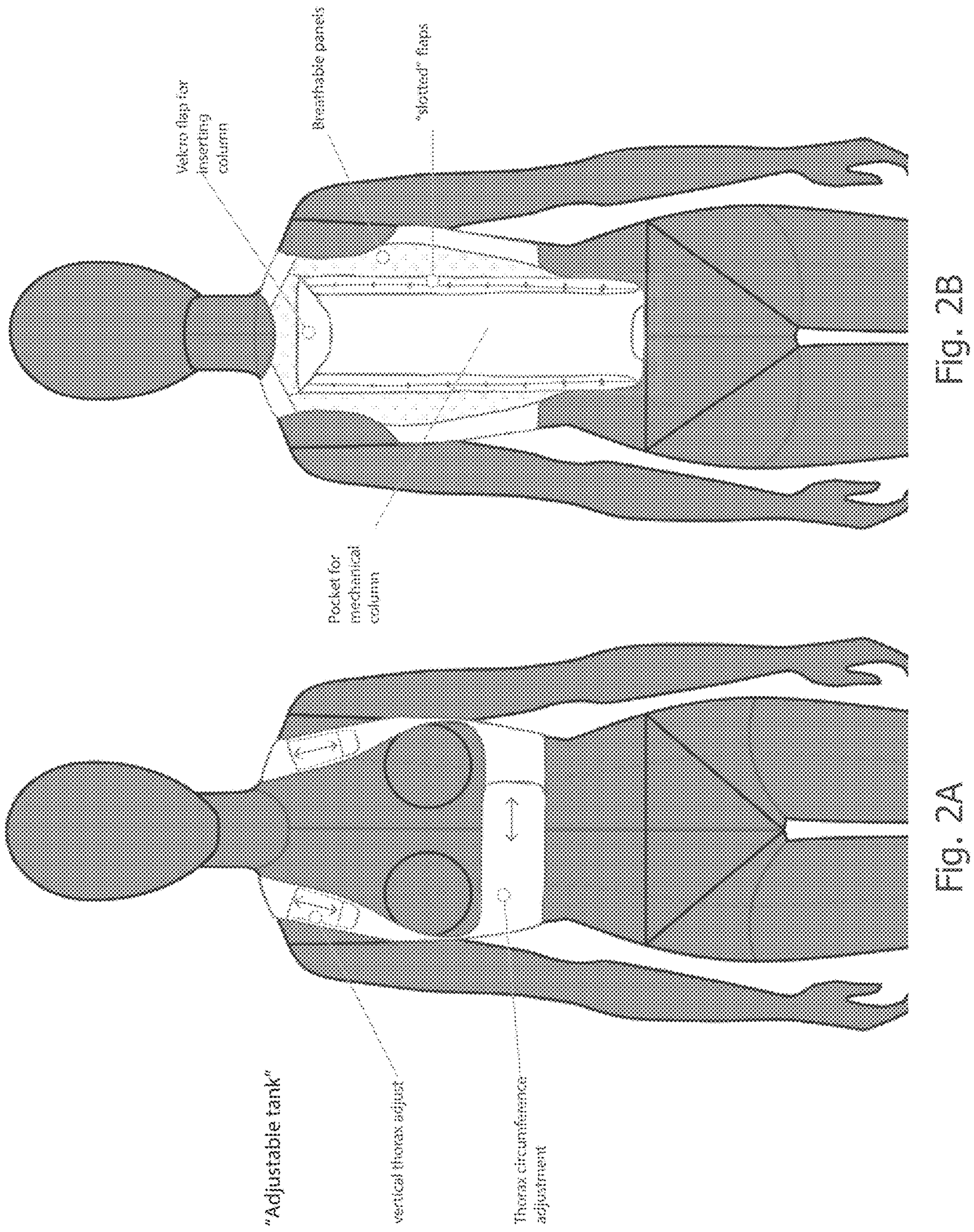
FIGS. 2A-2D depict embodiments of support systems.
Figure 2D:
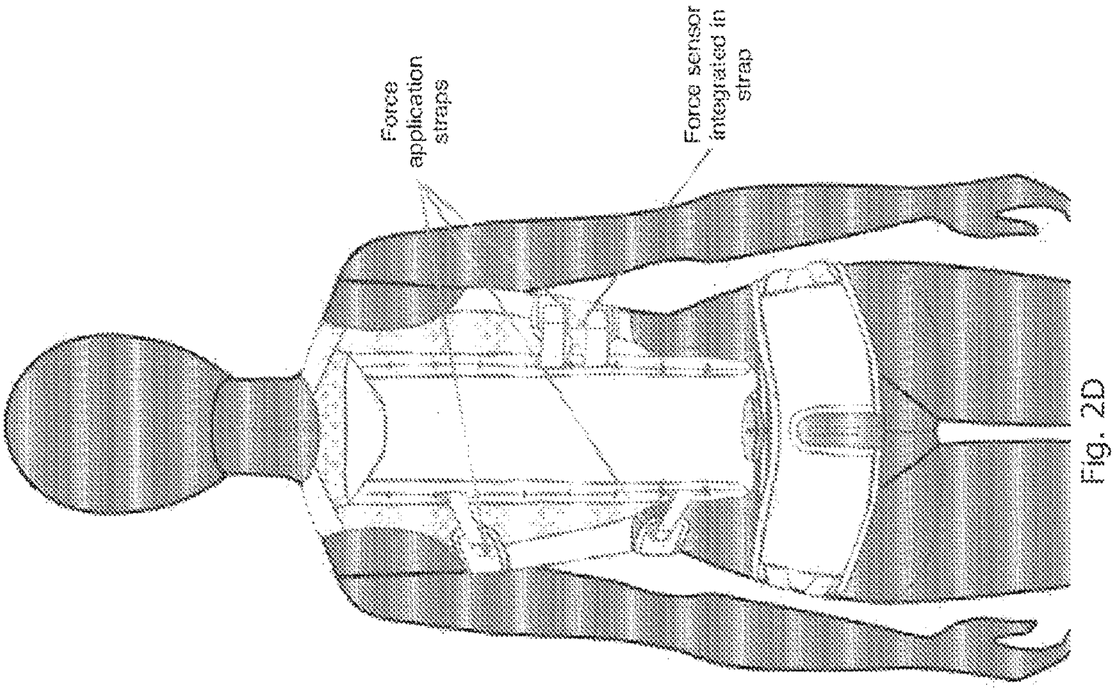
Figure 2C:
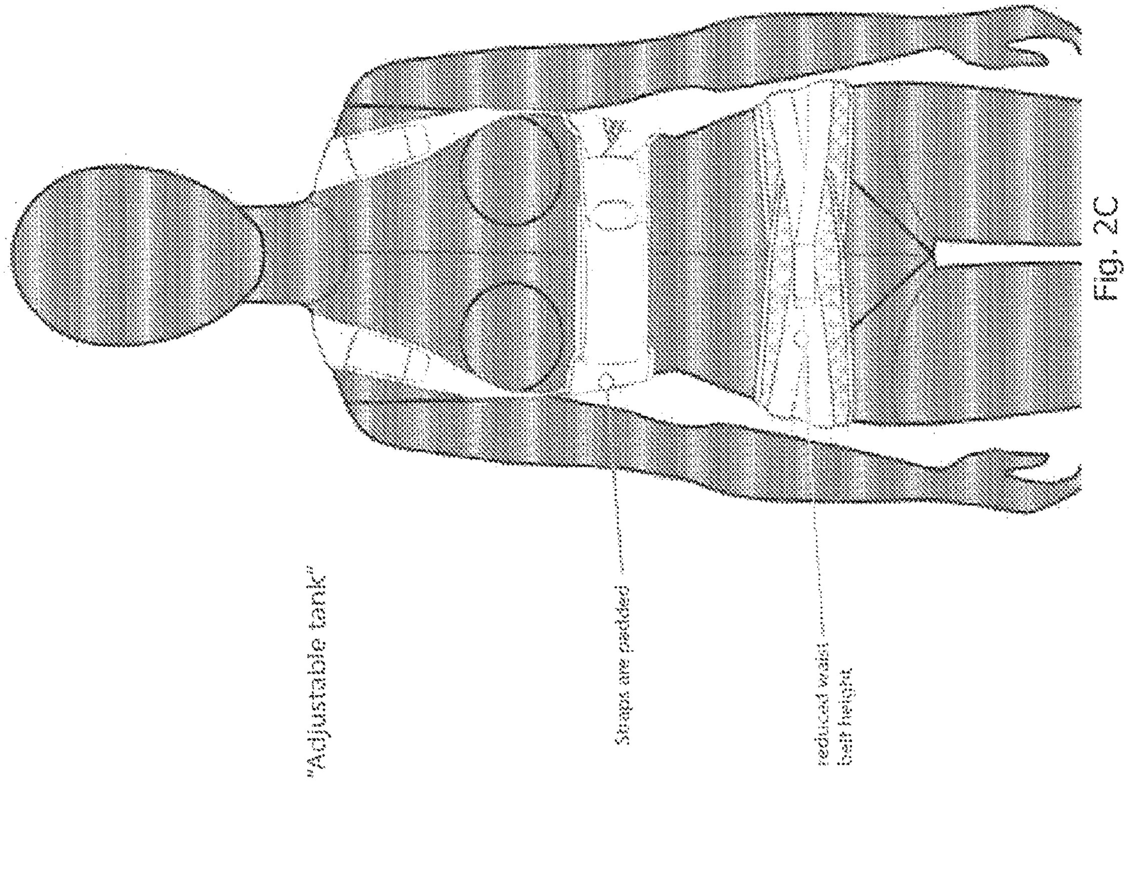

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments (e.g., walls may not be exactly orthogonal to one another in actual fabricated devices). Moreover, the drawings may only show the structures useful to understand the illustrated embodiments. Additional structures known in the art may not have been included to maintain the clarity of the drawings. For example, not every layer of a device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical, electrical, or magnetic/electromagnetic contact with each other and "coupled" may indicate elements co-operate or interact with each other, but they may or may not be in direct physical or electrical contact. Phrases such as "comprising at least one of A or B" include situations with A, B, or A and B.

Applicant determined noninvasive methods are usually more desirable but, depending on the condition being treated, have either limited success or require highly restrictive and painful external braces. Applicant further determined current rigid braces put exterior forces on the ribs of a subject, which restricts chest wall and spine motion and, in some instances, can lead to rib deformities. There are some flexible braces available which allow more freedom of movement. However, Applicant determined none of the known external braces appear to provide a distraction force to the spine and, specifically, a posterior distraction force and, in some instances, a posterior distraction force combined with a bending and torsional forces.

Therefore, Applicant determined a system and/or method which facilitate treatment of structural disorders of the spine without invasive techniques or unnecessarily restrictive braces would be highly desirable.

Examples are now addressed to better explain the composition and operation of embodiments shown in the figures or addressed herein.

Example 1 includes an external spinal brace system comprising a first vertebral segment (101); a first joint (104) that includes a first ball and socket joint; a second vertebral segment (102) that couples to the first vertebral segment via the first joint; a second joint (105) that includes a second ball and socket joint; a sacral segment (103) that couples to the second vertebral segment via the second joint. A sagittal plane (106) intersects the first and second vertebral segments, the first and second joints, and the sacral segment. A coronal plane (107) intersects one or more of the first and second vertebral segments, the first and second joints, and the sacral segment. The sacral segment includes first and second ratchets, the first ratchet comprising a first toothed rack (110) and a first spring-loaded finger (111) and the second ratchet comprising a second toothed rack (112) and a second spring-loaded finger (113). The first toothed rack includes a first outer surface (114) that is curved in the sagittal plane and the second toothed rack includes a second outer surface (115) that is curved in the sagittal plane.

Elements such as 101, 102 (sometimes referred to herein as vertebral segments or support members) are found within some or all of FIGS. 1, 4-13. Those figures at times address varying embodiments. While some embodiments may be preferred in certain situations, all such embodiments are viable embodiments and are the subject of the examples provided herein. The ratchets may be operated to increase distraction of the spine.

Example 2. The system of example 1, wherein the first outer surface is rigid and non-malleable.

Example 3. The system according to any of examples 1-2, wherein the second outer surface is rigid and non-malleable.

Example 4. The system according to any examples 1-3, wherein the first outer surface has a first center of curvature (116) and at least a portion of the first tooth rack is between the first outer surface and the first center of curvature.

The curvature helps increase comfort to the user of the system by better matching the sacral element to the user's back.

Example 5. The system according to any of examples 1-4 comprising a force sensor (117).

Example 6. The system of example 5, wherein the second joint is operatively coupled to the force sensor to convey force from the second joint to the force sensor.

Example 7. The system of example 6, wherein the second joint is slidingly coupled (FIG. 7) to the sacral segment.

Example 8. The system of example 7, wherein the second joint is not rigidly coupled to the force sensor or the sacral segment.

Example 9. The system of example 8, wherein the second joint has one of a male or female coupler (118, 119) and the sacral segment has another of the male or female coupler to slidingly and non-rigidly couple to the second joint's one of the male or female coupler.

Example 10. The system of example 7, wherein the first toothed rack includes a void (120) proportioned to receive the force sensor.

Example 11. The system of example 7, wherein the force sensor is included within the void.

Example 12. The system according to any of examples 1-11, wherein the first toothed rack is slidingly coupled to the second toothed rack.

Example 13. The system according to any of examples 1-12 comprising: first opposing support members (121, 122) on opposing lateral sides of the first vertebral segment; and second opposing support members (123, 124) on opposing lateral sides of the second vertebral segment.

Another version of example 13. The system according to any of examples 1-12 comprising: a first number of support members (121, 123) on a first lateral side of the first vertebral segment; and a second number of support members (122) on a second lateral side of the first vertebral segment. The first and second lateral sides are on opposite sides of the first vertebral segment. The first number is unequal to the second number. A total number of support members are arranged asymmetrically to the first vertebral segment.

Example 13a. A system of example 13, wherein the system is configured to provide a bending force to a patient's spine.

Example 13b. A system of example 13, wherein the system is configured to provide a torsional force to a patient's spine.

Example 13c. A system of example 13, wherein the system is configured to provide a torsional force to a patient's spine and a bending force to the patient's spine.

Example 14. The system of example 13 comprising a top brace member (125) and a bottom brace member (126). The sacral segment and the first and second opposing support members are all between the top and bottom brace members.

Example 15. The system of example 14 wherein the first ratchet is configured to increase the distance between the top and bottom brace members and consequently provide a distraction force to a user of the system.

Example 16. The system of example 14 wherein the first ratchet is configured to increase the distance between the top and bottom brace members and consequently provide a posterior distraction force to a user of the system.

The number of support members (123, 124) may be determined at least in part by the size of the individual support members and a length of a subject's torso. The location of the support members will be determined by the deformity of the spine that needs to be corrected. The number of support members may be adjusted for a subject as needed (e.g., as a subject grows support members as well as vertebral segments 101, 102 may be added).

In some embodiments, the system may include a coupling system including some combination of elements/support members 101, 102, 103, 121, 122, 123, 124, 125, 126. The coupling system may couple (or directly attach) the plurality of support members to a subject such that the plurality of support members is positioned, during use, along at least a portion of the subject's spine on the surface of the subject. In some embodiments, the coupling system may include a plurality of elongated members 121, 122 coupled (or directly attached) to the plurality of support members 101, 102, 103. The plurality of elongated members may be coupled (or directly attached) to opposing sides of the plurality of support members 101, 102, 103. The plurality of elongated members may be coupled (or directly attached) to the same side, alternating sides, or opposite sides of adjacent support members. The plurality of elongated members may wrap around the subject in order to couple (or directly attach) the system to the subject during use. A length of the plurality of support members may be adjustable relative to the plurality of support members. The length may be adjustable using buckles, loops, etc. The ability to adjust the length may be beneficial for sizing the system for each individual subject, for making adjustments to forces applied by the elongated members to treatment as a subject's condition changes. It also allows for adjustments to accommodate growth of a subject.

Figure 3B:
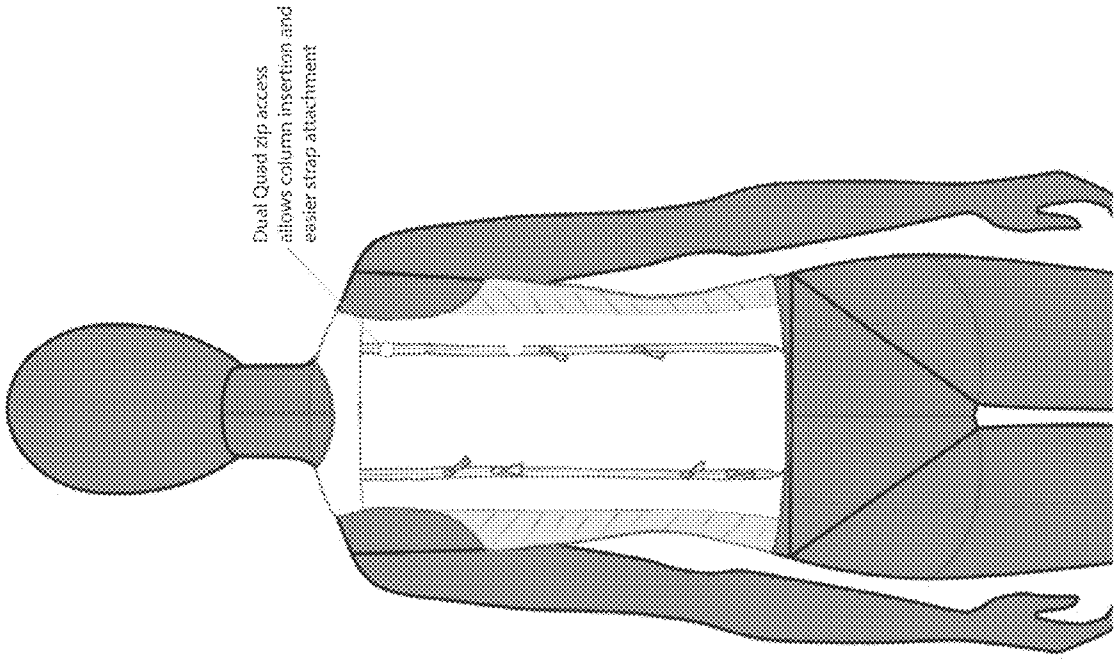
FIGS. 3A-3D depict embodiments of support systems.
Figure 3A:
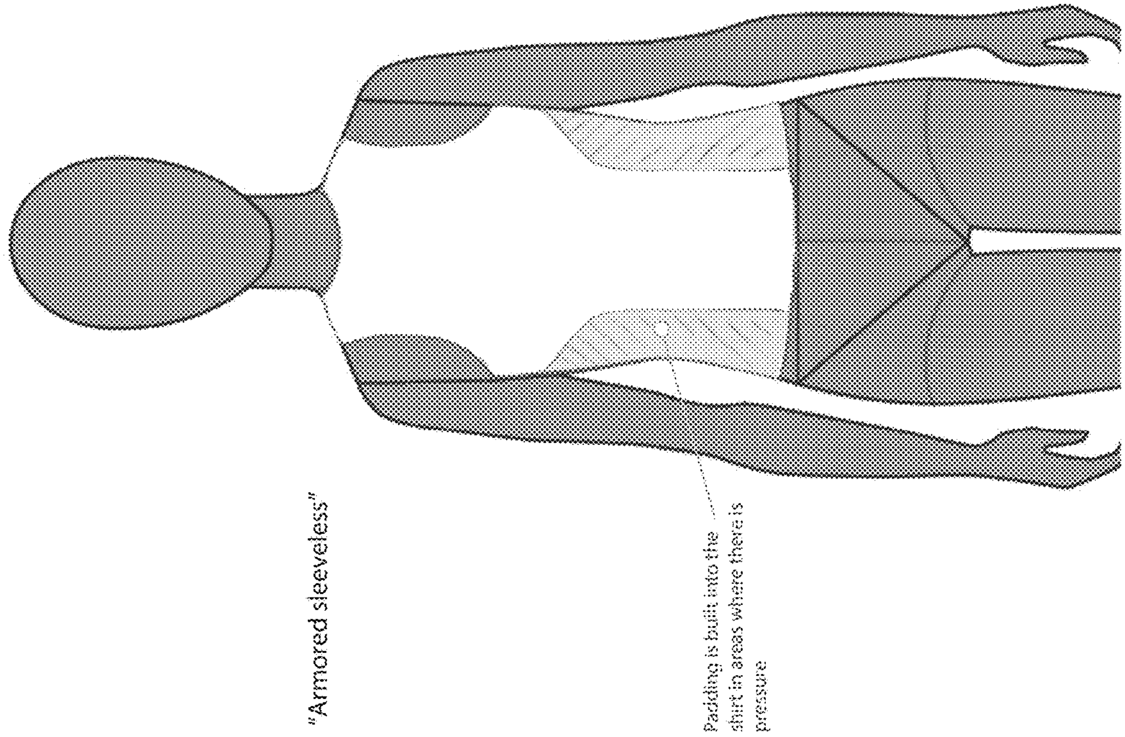
Figure 3D:
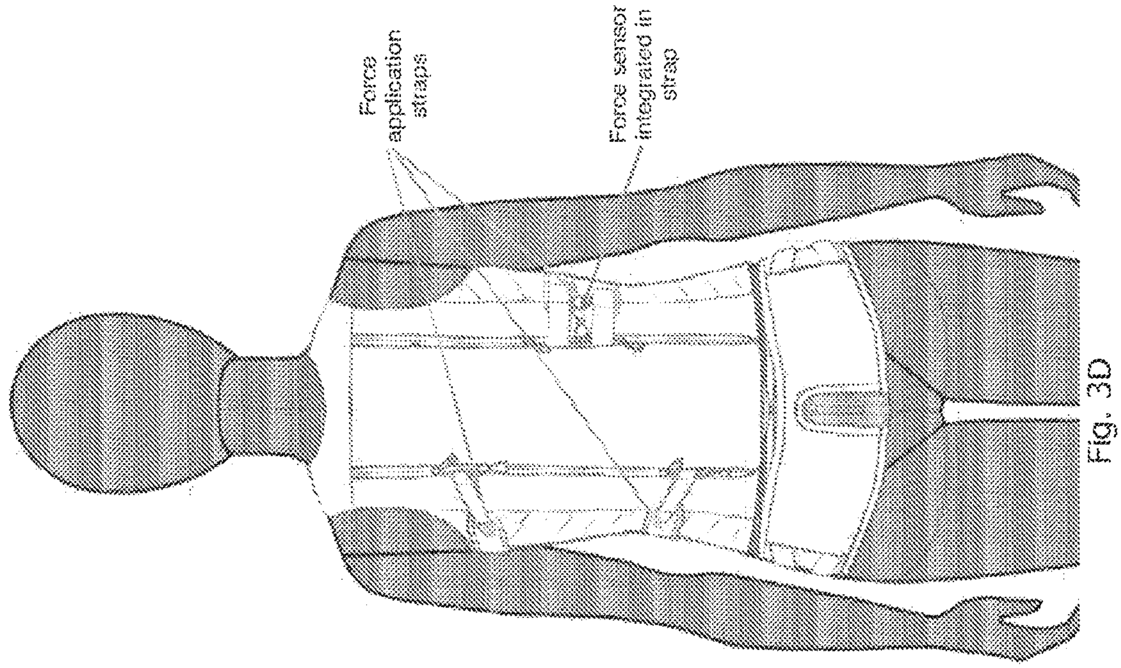
Figure 3C:
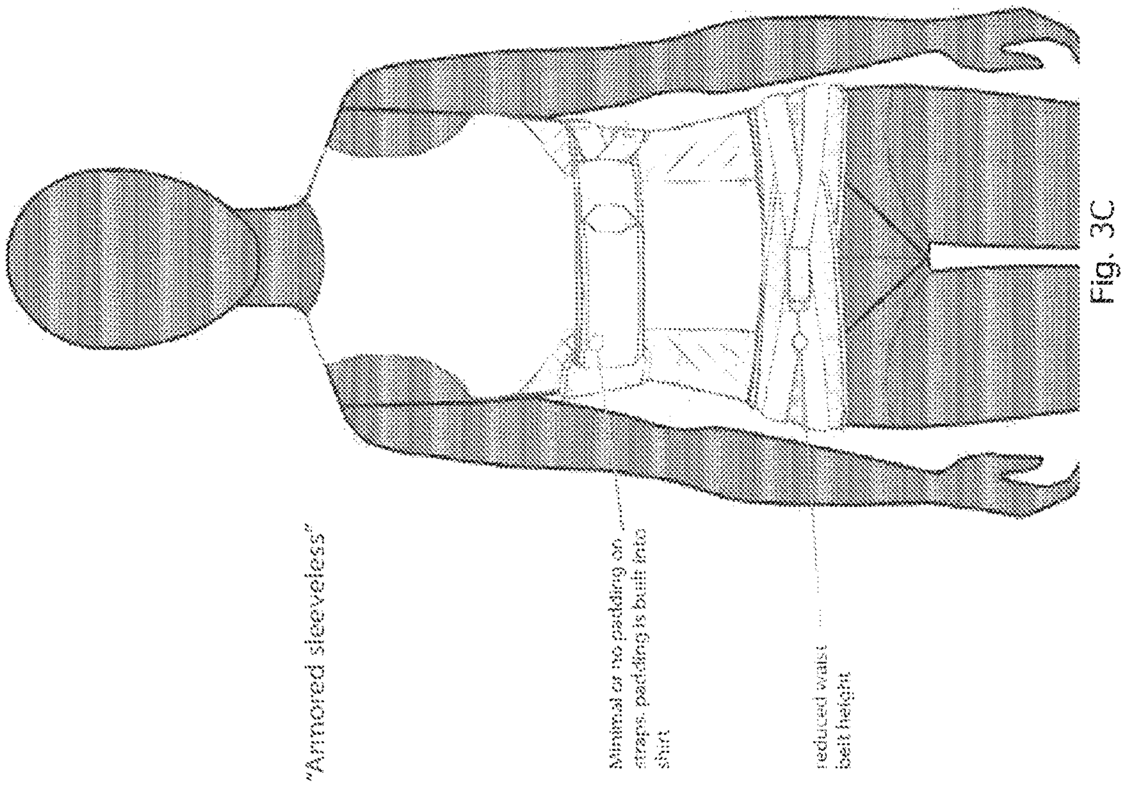
Figure 4:
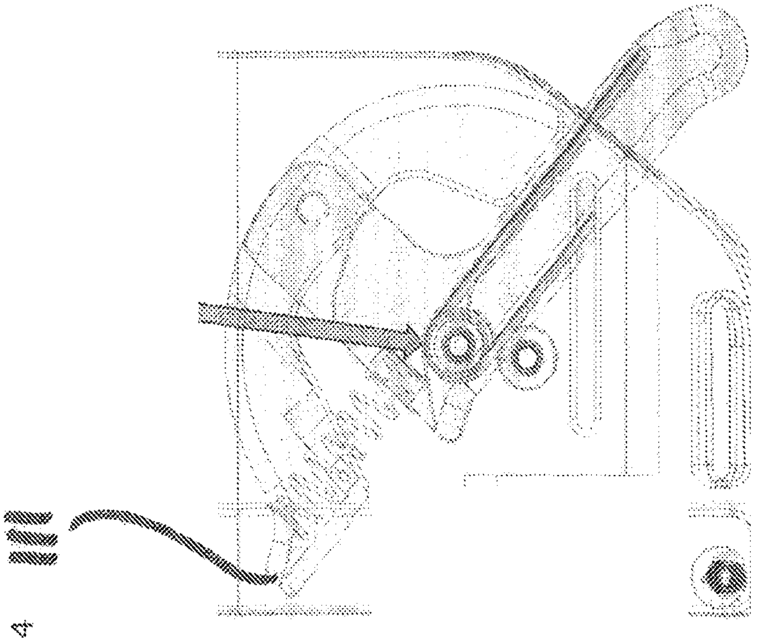
FIG. 4 depicts an embodiment of a portion of a ratchet system.
Figure 5:
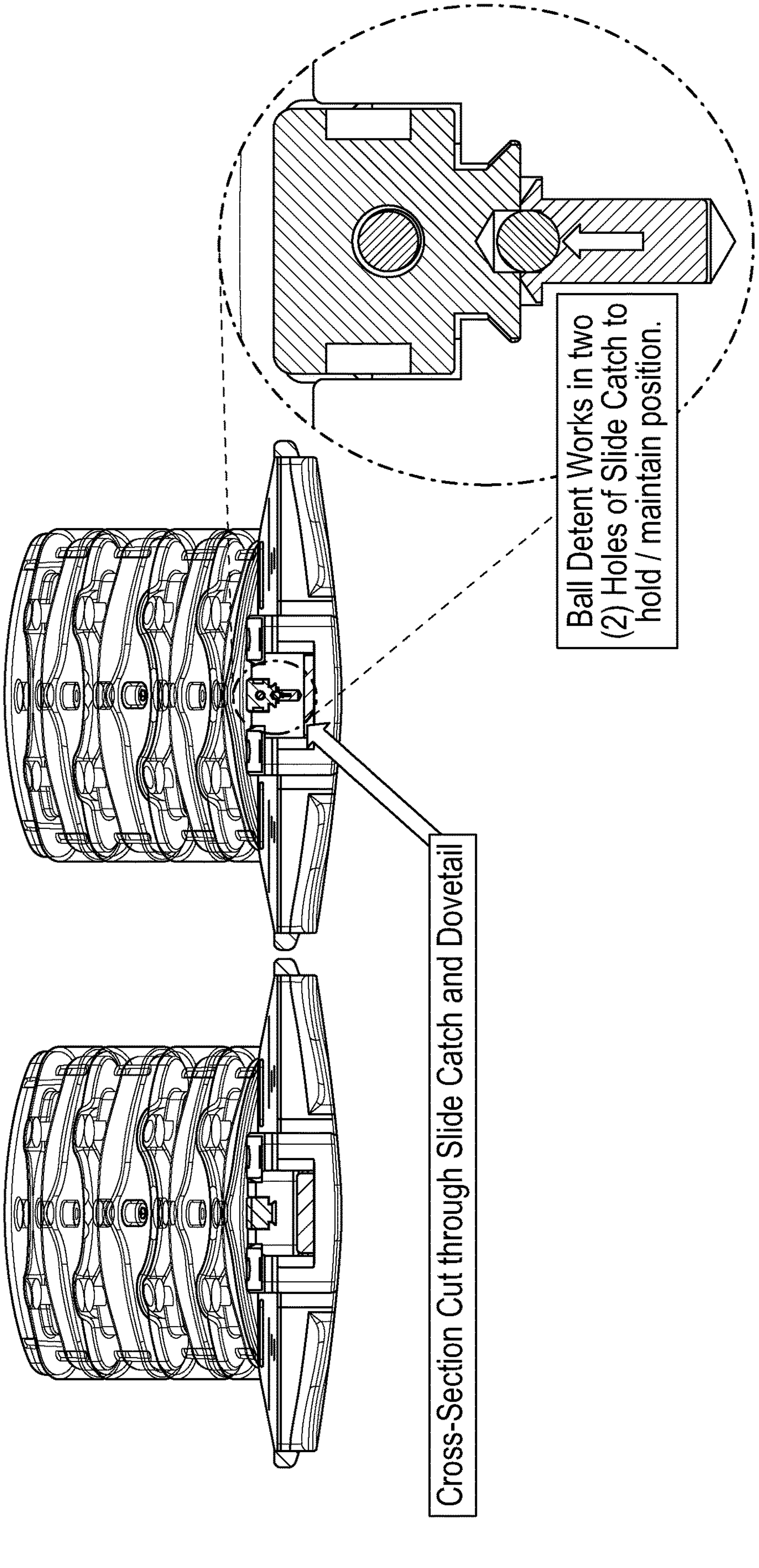
FIG. 5 depicts an embodiment of a portion of a locking system.
Figure 6:
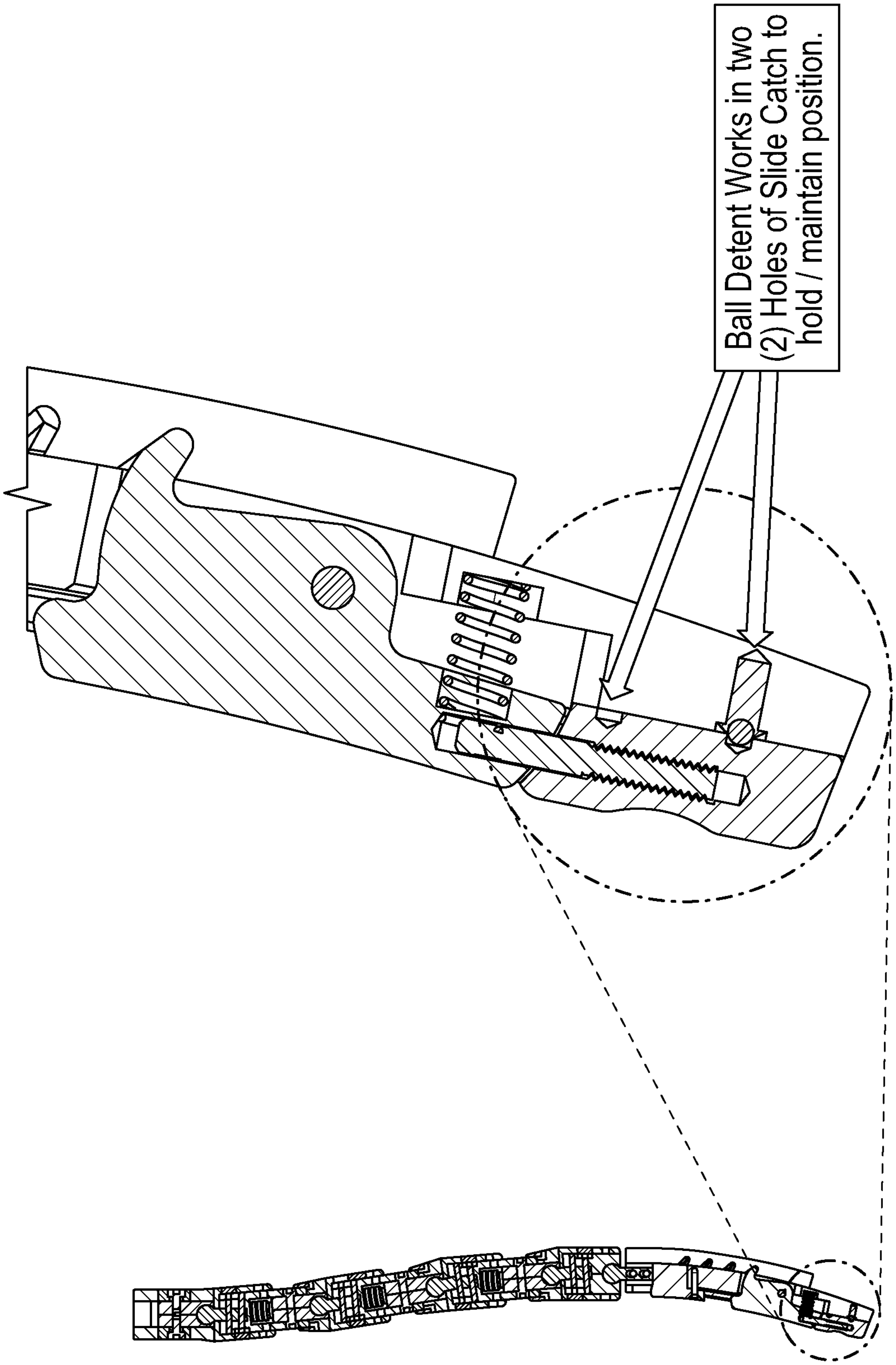
FIG. 6 depicts an embodiment of a portion of a locking system.
Figure 7:
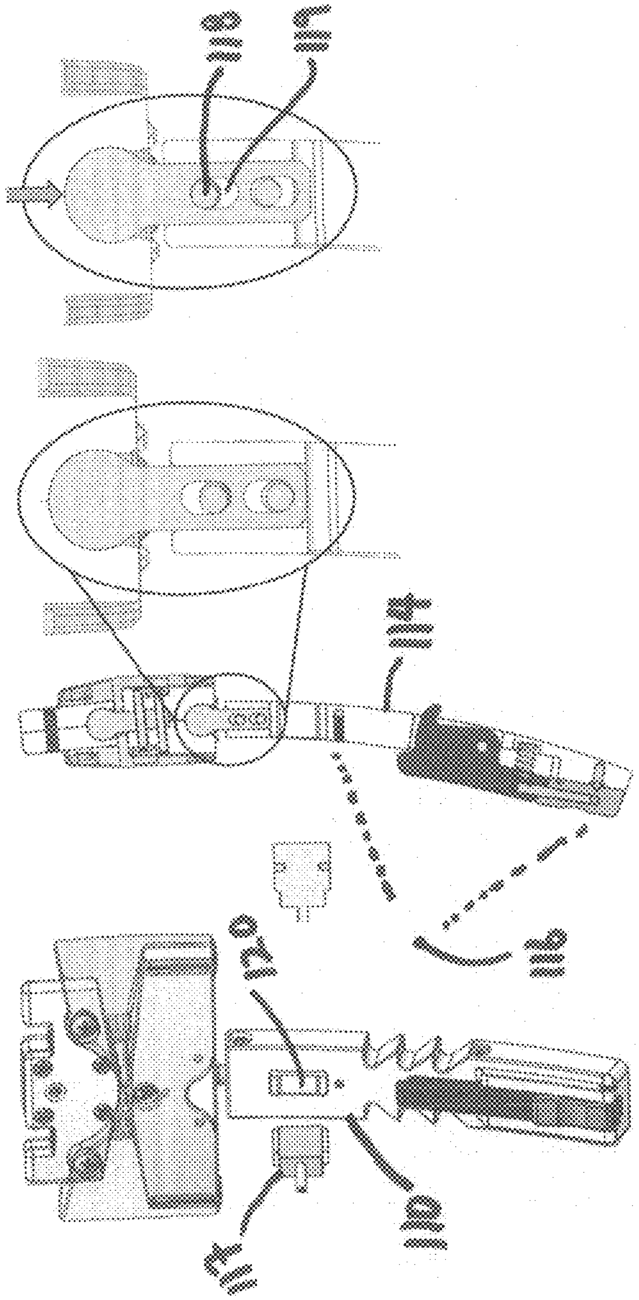
FIG. 7 depicts an embodiment of a portion of a spinal support system.
Figure 8:
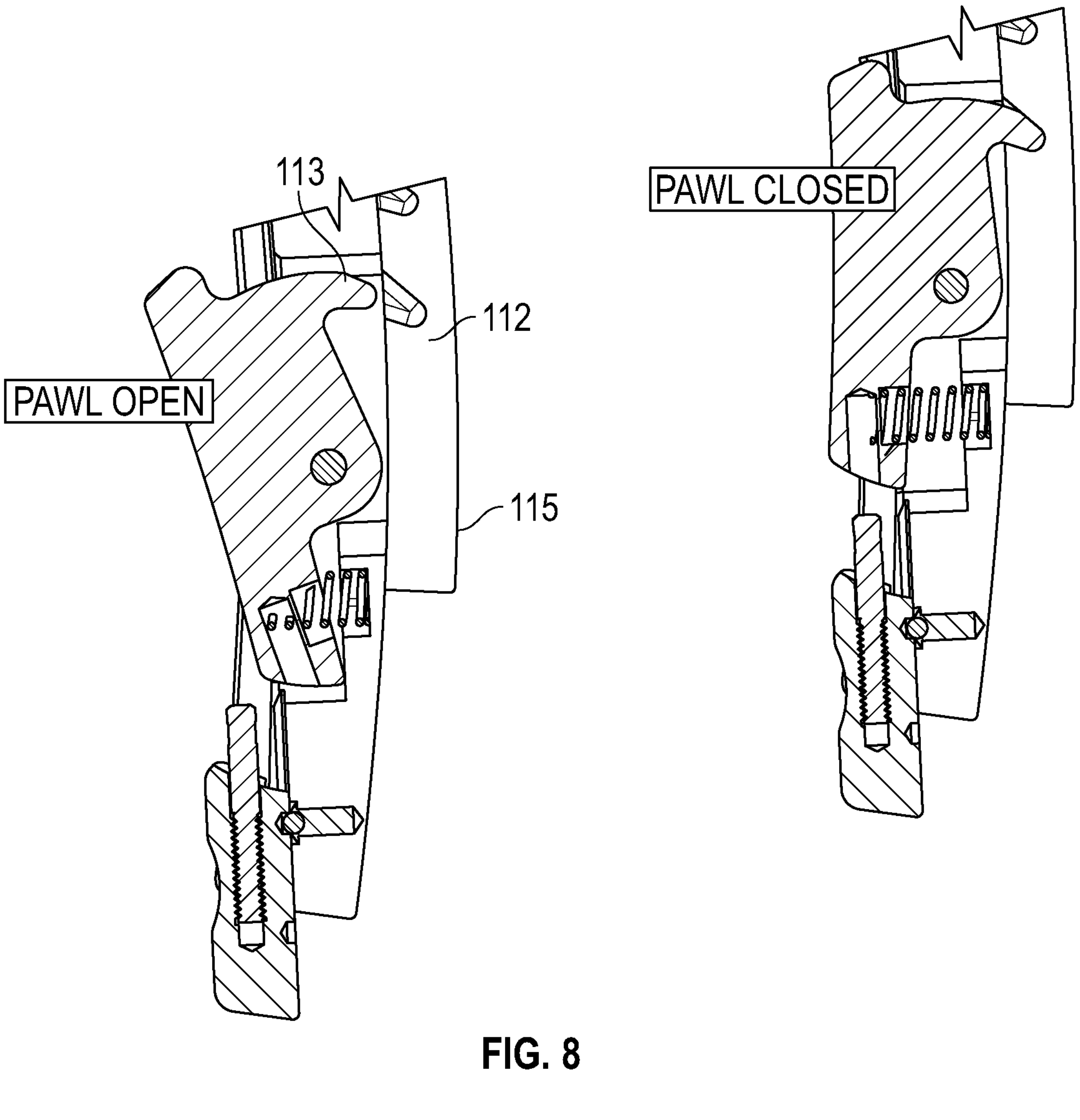
FIG. 8 depicts an embodiment of a portion of a locking system.
Figure 9:
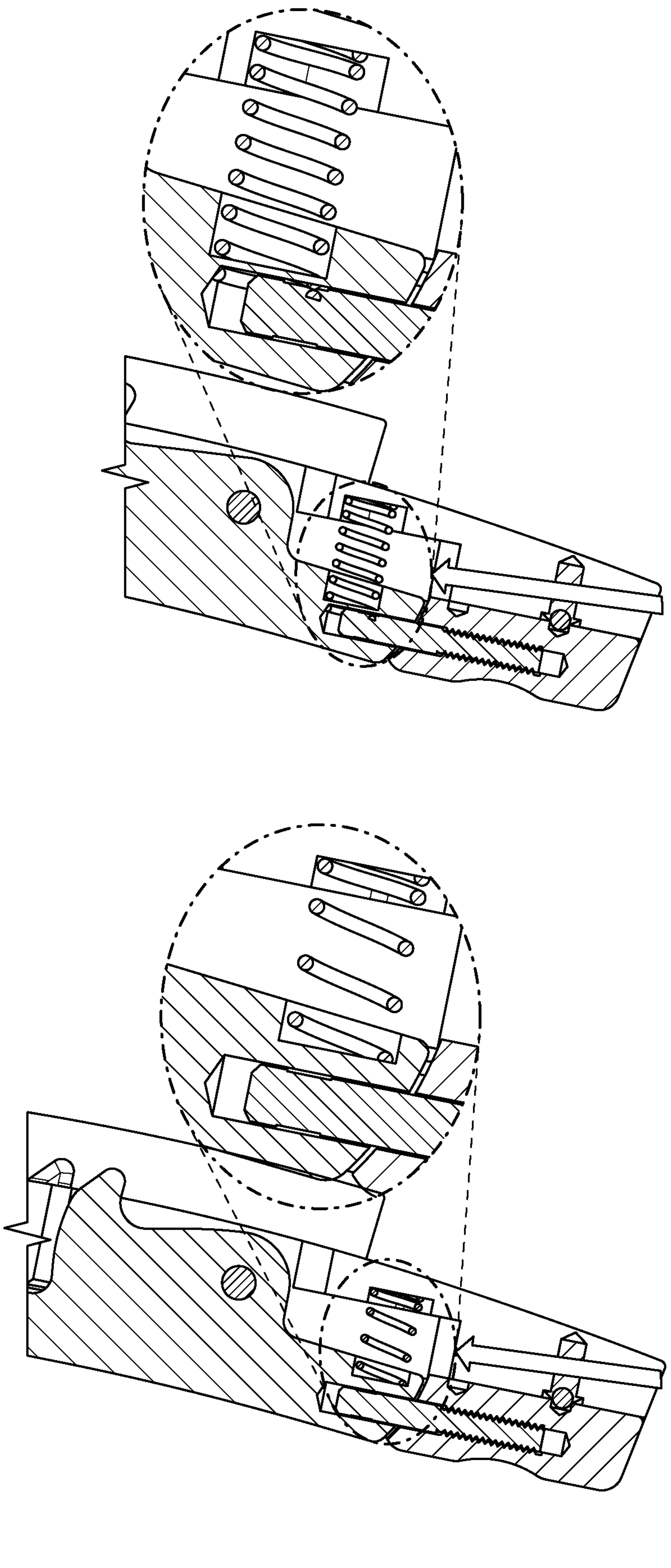
FIG. 9 depicts an embodiment of a portion of a locking system.
Figure 10:
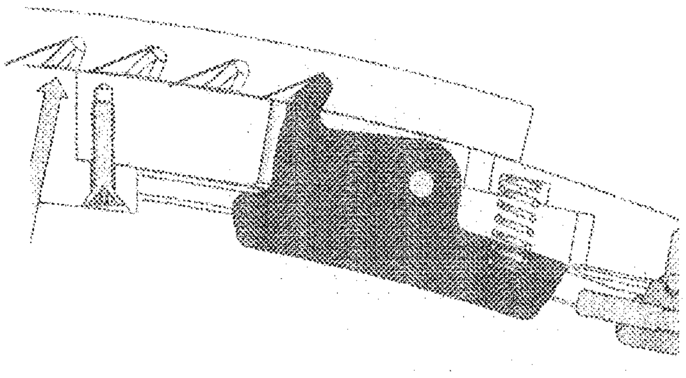
FIG. 10 depicts an embodiment of a portion of a locking system.

In some embodiments, the system may include one or more coupling elongated members 125, 126 (e.g., similar to a belt) which functions to couple (or directly attach) the system to a subject during use. An upper elongated member 125 may function to couple (or directly attach) the system to an upper portion under a subject's armpits or below the subject's shoulder blades. A lower elongated member 126 may function to couple (or directly attach) the system to a lower portion of a subject. The lower elongated member may be positioned at a subject's waist at and/or above the subject's pelvis. The coupling elongated members may be formed from substantially flexible and/or rigid materials. In some embodiments, the upper elongated member is positioned, during use, around an upper portion of the subject's torso and the lower elongated member is positioned, during use, around a lower portion of the subject's torso. As mentioned above, members 125, 126 may include belts or other means to attach the system to the user. For example, FIGS. 2A through 3D show means for attaching a system to a user. For example, FIG. 3C-3D show various straps, panels, belts, and the like and general clothing (shirts, vests, tanks) to fix a brace to a user.

Example 17. The system according to any of examples 1-16, wherein when the system is coupled to a user the sagittal plane intersects at least a portion of the user's spine.

Example 18. The system according to any of examples 1-17, wherein the first toothed rack includes a void and the void includes at least a portion of the second spring-loaded finger.

Example 19. The system according to any of examples 1-17, wherein the first toothed rack includes a void and the void includes at least a portion of at least one of the second spring-loaded finger, the second toothed rack, or combinations thereof.

Another version of example 1. An external spinal brace system comprising: a first vertebral segment (101); a first joint (104); a second vertebral segment (102) that couples to the first vertebral segment via the first joint; a second joint (105); a sacral segment (103) that couples to the second vertebral segment via the second joint. A sagittal plane (106) intersects the first and second vertebral segments, the first and second joints, and the sacral segment. A coronal plane (107) intersects one or more of the first and second vertebral segments, the first and second joints, and the sacral segment. The sacral segment includes first and second ratchets, the first ratchet comprising a first toothed rack (110) and a first spring-loaded finger (111) and the second ratchet comprising a second toothed rack (112) and a second spring-loaded finger (113). The first tooth rack includes a first outer surface (114) that is curved in the sagittal plane and the second tooth rack includes a second outer surface (115) that is curved in the sagittal plane.

Thus, in some embodiments not all joints are ball and socket joints but may instead be other joints (e.g., hinge) that provide varying degrees of freedom.

Another version of example 1. An external spinal brace system comprising: a first vertebral segment (101); a first joint (104); a second vertebral segment (102) that couples to the first vertebral segment via the first joint; a second joint (105); a sacral segment (103) that couples to the second vertebral segment via the second joint. A sagittal plane (106) intersects the first and second vertebral segments, the first and second joints, and the sacral segment. A coronal plane (107) intersects one or more of the first and second vertebral segments, the first and second joints, and the sacral segment. The sacral segment includes first and second ratchets. The first ratchet includes a first outer surface (114) that is curved in the sagittal plane and the second ratchet includes a second outer surface (115) that is curved in the sagittal plane.

Thus, in some embodiments not all ratchets include spring-biased fingers and the like.

Another version of example 1. An external spinal brace system comprising: a first vertebral segment (101); a first joint (104) that includes a first ball and socket joint; a second vertebral segment (102) that couples to the first vertebral segment via the first joint; a second joint (105) that includes a second ball and socket joint; a sacral segment (103) that couples to the second vertebral segment via the second joint. A sagittal plane (106) intersects the first and second vertebral segments, the first and second joints, and the sacral segment. A coronal plane (107) intersects one or more of the first and second vertebral segments, the first and second joints, and the sacral segment. The sacral segment includes a first ratchet, the first ratchet comprising a first toothed rack (110) and a first spring-loaded finger. The first toothed rack includes a first outer surface (114) that is curved in the sagittal plane.

Thus, not all embodiments include multiple ratchets.

Example 1a. An external spinal brace system comprising: a first vertebral segment (101); a first joint (104); a second vertebral segment (102) that couples to the first vertebral segment via the first joint; a second joint (105); and a sacral segment (103) that couples to the second vertebral segment via the second joint. A first plane (106) intersects the first and second vertebral segments, the first and second joints, and the sacral segment. A second plane (107), which is orthogonal to the first plane, intersects one or more of the first and second vertebral segments, the first and second joints, and the sacral segment. The sacral segment includes first and second ratchets, the first ratchet comprising a first toothed rack (110) and a first lever (111) and the second ratchet comprising a second toothed rack (112) and a second lever (113). The first tooth rack includes a first outer surface (114) and the second tooth rack includes a second outer surface (115). At least one of the first or second outer surfaces is curved in the first plane.

Example 2a. The system of example 1a, wherein both of the first and second outer surfaces are curved in the first plane.

Example 3a. The system according to any of examples 1a-2a, wherein (a) the second outer surface is rigid and non-malleable, and (b) the first outer surface is rigid and non-malleable.

Example 4a. The system according to any examples 1a-3a, wherein the first outer surface has a first center of curvature (116) and at least a portion of the first tooth rack is between the first outer surface and the first center of curvature.

Example 5a. The system according to any of examples 1a-4a comprising a force sensor (117).

Example 6a. The system of example 5a, wherein the second joint is operatively coupled to the force sensor to convey force from the second joint to the force sensor.

Example 7a. The system according to any of examples 1a-6a, wherein the second joint is slidingly coupled (FIG. 7) to the sacral segment.

Example 8a. The system of example 6a, wherein the second joint is not rigidly coupled to the force sensor or the sacral segment.

Example 9a. The system of example 8a, wherein the second joint has one of a male or female coupler (118, 119) and the sacral segment has another of the male or female coupler to slidingly and non-rigidly couple to the second joint's one of the male or female coupler.

Example 10a. The system of example 6a, wherein the first toothed rack includes a void (120) proportioned to receive the force sensor.

Example 11a. The system of example 10a, wherein the force sensor is included within the void.

Example 12a. The system according to any of examples 1a-11a, wherein the first toothed rack is slidingly coupled to the second toothed rack.

Another version of 12a. The system according to any of examples 1a-11a, wherein the first toothed rack is slidingly coupled to the second toothed rack; and the first toothed rack is directly contacting the second toothed rack.

Example 13a. The system according to any of examples 1a-12a comprising: first opposing support members (121, 122) on opposing lateral sides of the first vertebral segment; and second opposing support members (123, 124) on opposing lateral sides of the second vertebral segment.

Another version of example 13a. The system according to any of examples 1-12 comprising: a first number of support members (121, 123) on a first lateral side of the first vertebral segment; and a second number of support members (122) on a second lateral side of the first vertebral segment. The first and second lateral sides are on opposite sides of the first vertebral segment. The first number is unequal to the second number. A total number of support members are arranged asymmetrically to the first vertebral segment.

Example 13a'. A system of example 13a, wherein the system is configured to provide a bending force to a patient's spine.

Example 13b'. A system of example 13a, wherein the system is configured to provide a torsional force to a patient's spine.

Example 13c'. A system of example 13a, wherein the system is configured to provide a torsional force to a patient's spine and a bending force to the patient's spine.

Example 14a. The system of example 13a comprising a top brace member (125) and a bottom brace member (126), wherein the sacral segment and the first and second opposing support members are all between the top and bottom brace members.

Example 15a. The system of example 14a wherein the first ratchet is configured to increase the distance between the top and bottom brace members and consequently provide a distraction force to a user of the system.

Example 16a. The system of example 14a wherein the first ratchet is configured to increase the distance between the top and bottom brace members and consequently provide a posterior distraction force to a user of the system.

Example 17a. The system according to any of examples 1a-16a, wherein when the system is coupled to a user the first plane intersects at least a portion of the user's spine.

Example 18a. The system according to any of examples 1a-17a, wherein the first toothed rack includes a void and the void includes at least a portion of the second lever.

Example 19a. The system according to any of examples 1a-17a, wherein the first toothed rack includes a void and the void includes at least a portion of at least one of the second lever and the second toothed rack.

Example 20a. The system according to any of examples 1a-19a, comprising a lock to lock the second toothed rack into a static position.

Example 21a. The system according to any of examples 1a-20a, wherein the second plane does not intersect each of the first and second vertebral segments, the first and second joints, and the sacral segment.

Another version of 1a. An external spinal brace system comprising: a first vertebral segment (101); a first joint (104); a second vertebral segment (102) that couples to the first vertebral segment via the first joint; a second joint (105); and a sacral segment (103) that couples to the second vertebral segment via the second joint. A first plane (106) intersects the first and second vertebral segments, the first and second joints, and the sacral segment. A second plane (107), which is orthogonal to the first plane, intersects one or more of the first and second vertebral segments, the first and second joints, and the sacral segment. The sacral segment includes a first ratchet, the first ratchet comprising a first toothed rack (110) and a first lever (111). The first tooth rack includes a first outer surface (114); wherein the first outer surface is curved in the first plane.

Thus, not all embodiments include multiple ratchets.

Example 1b. An external spinal brace system comprising: a first vertebral segment (201); a first joint (204) that includes a first ball and socket joint; a second vertebral segment (202) that couples to the first vertebral segment via the first joint; a second joint (205), which includes a second ball and socket joint, coupled to the second vertebral segment; and a first bushing (231) between the first and second vertebral segments. A sagittal plane (206) intersects the first and second vertebral segments, the first and second joints, and the first bushing. A coronal plane (207) intersects one or more of (b)(i) the first and second vertebral segments, (b)(ii) the first and second joints, and (b)(iii) the first bushing. The first bushing includes a superior surface (232) disposed in a first plane of the first bushing and an inferior surface (233) disposed in a second plane of the first bushing. The first plane of the first bushing is not parallel to the second plane of the first bushing.

Figure 14D:
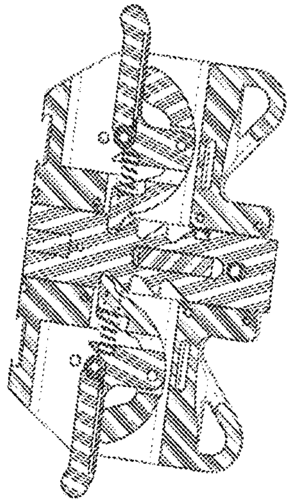
FIGS. 14A-21D depict an embodiment of a portion of a spinal support system in varying stages of distraction.
FIG. 14B shows the embodiment in a locked stage preventing any change in distraction.
Figure 14C:
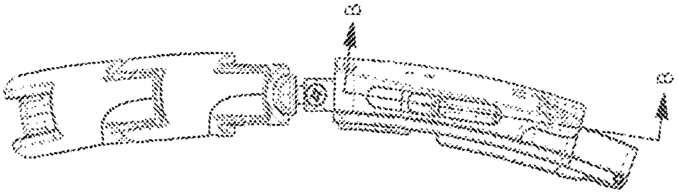
Figure 14B:
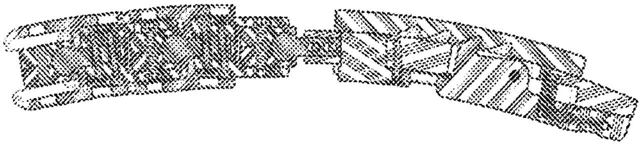
Figure 14A:
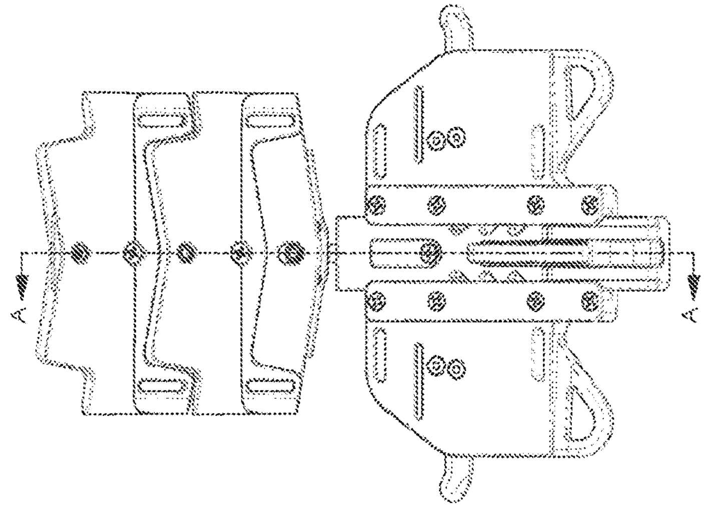
Figure 15D:
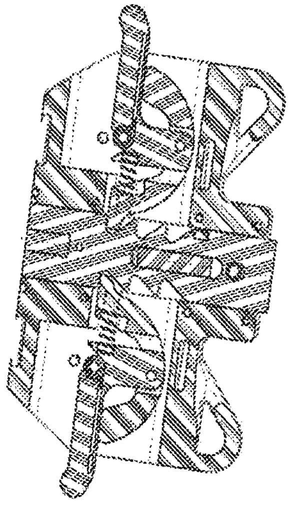
FIG. 15B shows the embodiment unlocked and ready for a change in distraction.
Figure 15C:
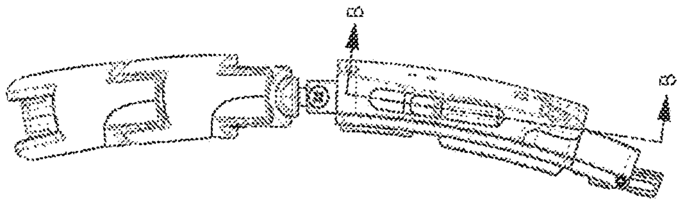
Figure 15B:
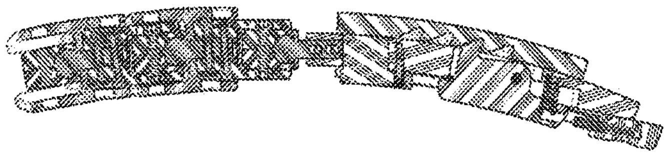
Figure 15A:
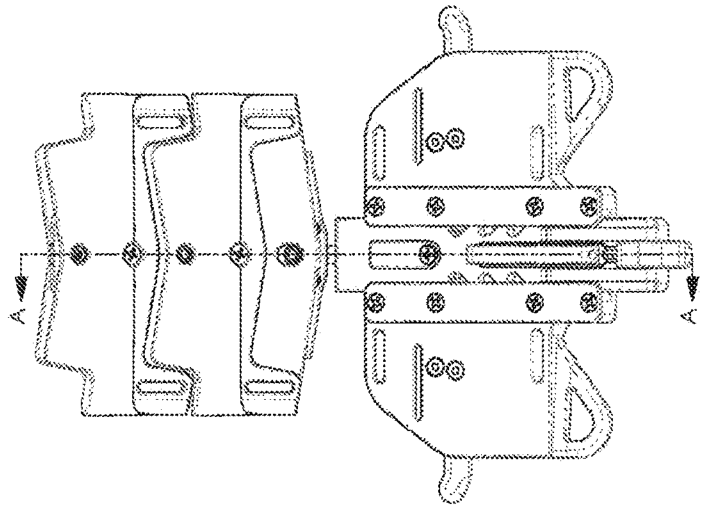
Figure 16A:
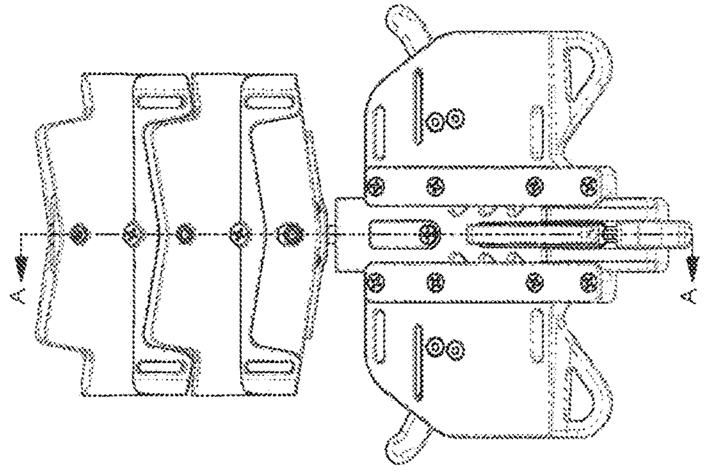
FIG. 16D shows the initial change in ratcheting to produce a change in distraction along the user's spinal column.
Figure 16B:
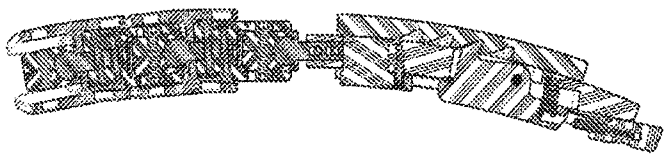
Figure 16C:
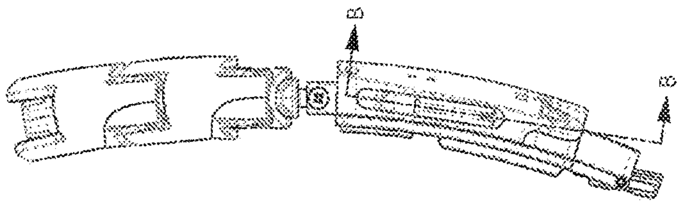
Figure 16D:
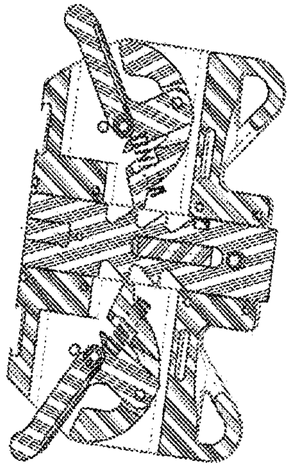
Figure 17A:
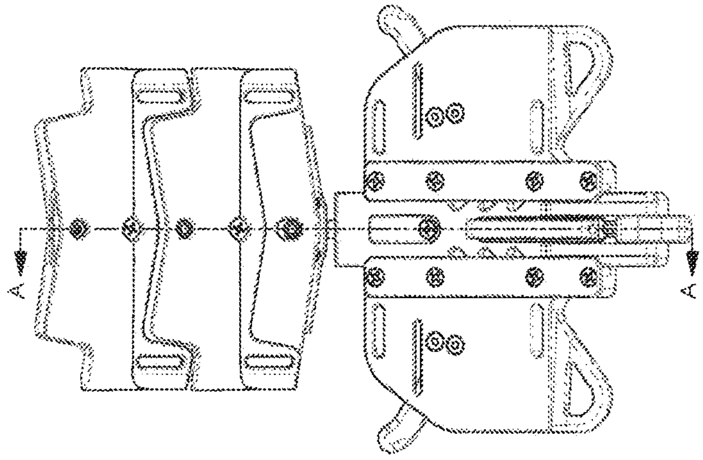
Figure 17B:
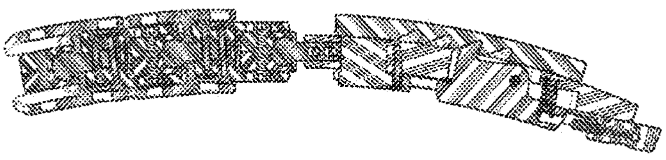
Figure 17C:
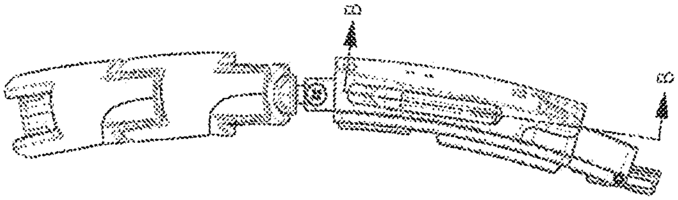
Figure 17D:
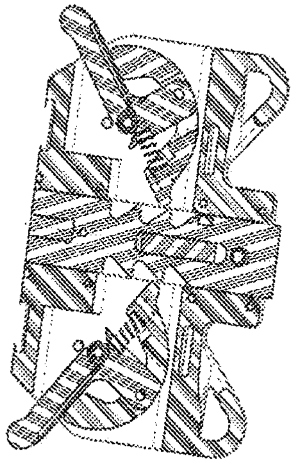
Figure 18D:
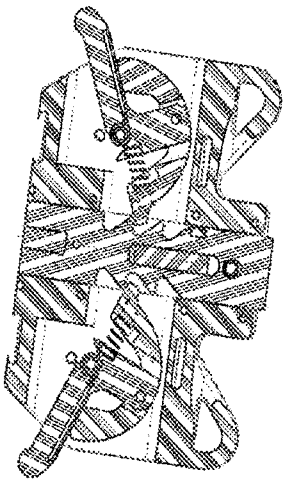
Figure 18C:
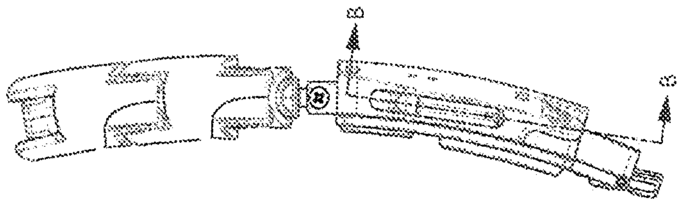
Figure 18B:
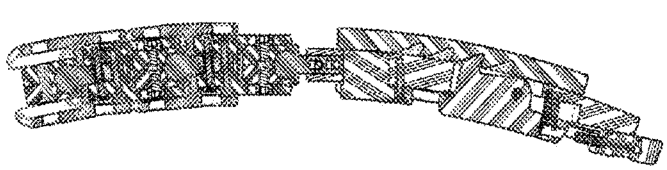
Figure 18A:
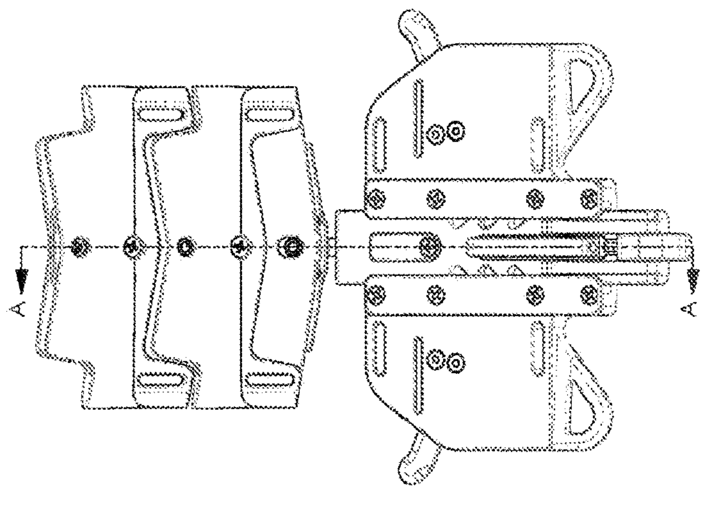
Figure 19D:
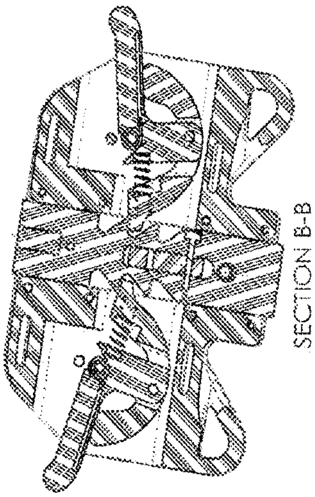
Figure 19C:
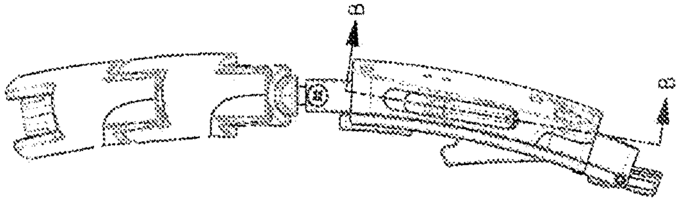
Figure 19B:
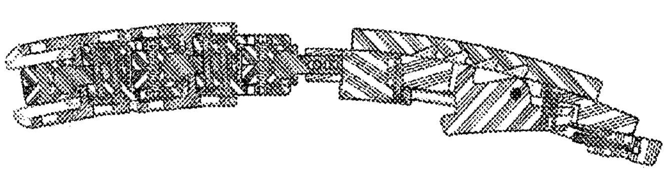
Figure 19A:
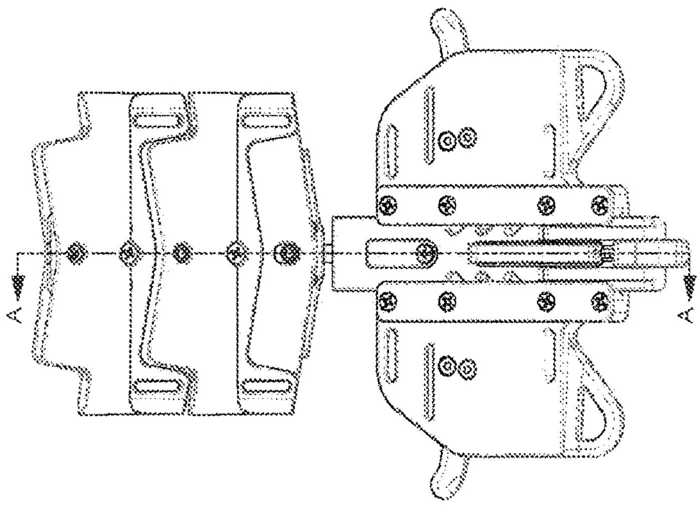
Figure 20D:
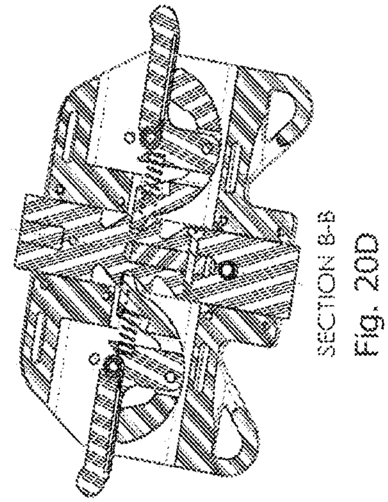
FIG. 20D shows the completion of a step of increasing distraction and FIG. 21B shows the increased distraction being locked in place.
Figure 20C:
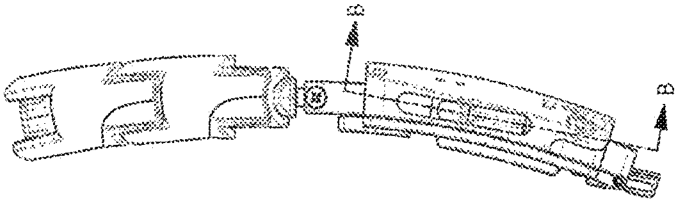
Figure 20B:
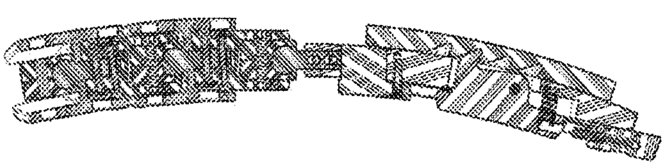
Figure 20A:
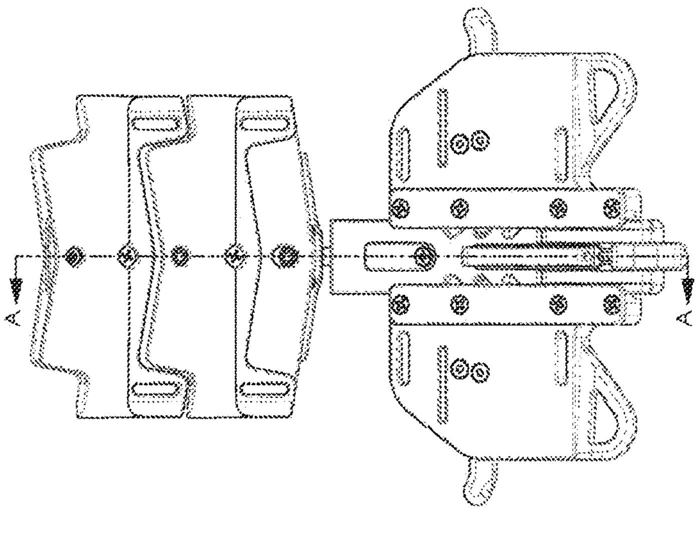
Figure 21A:
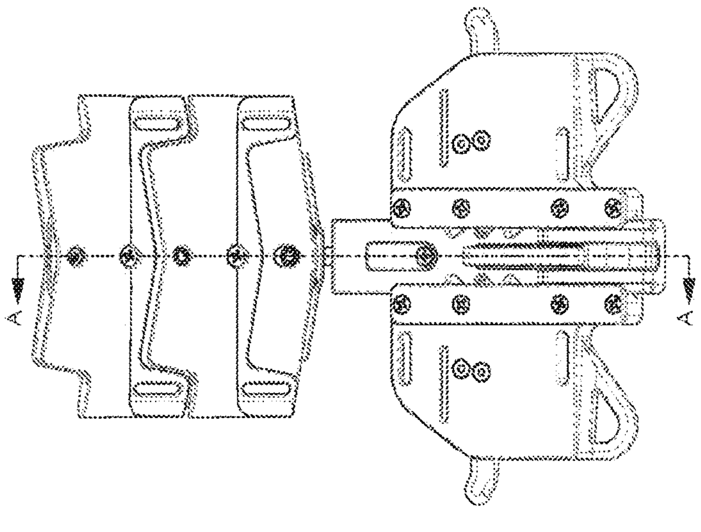
Figure 21B:
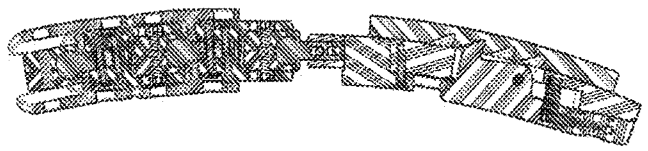
Figure 21C:
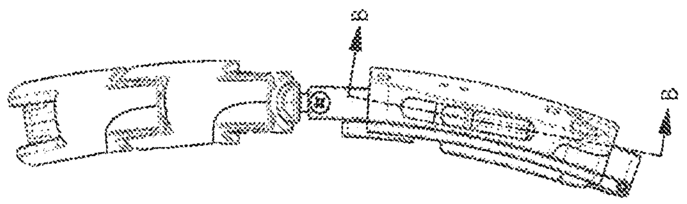
Figure 21D:
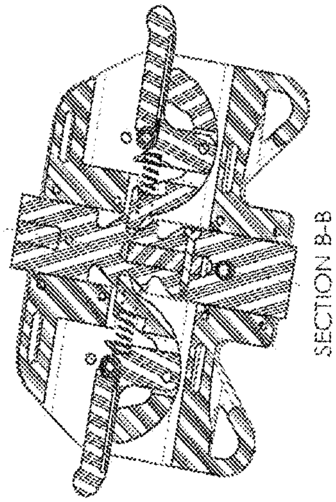
Figures 30A, 30B, 30C:
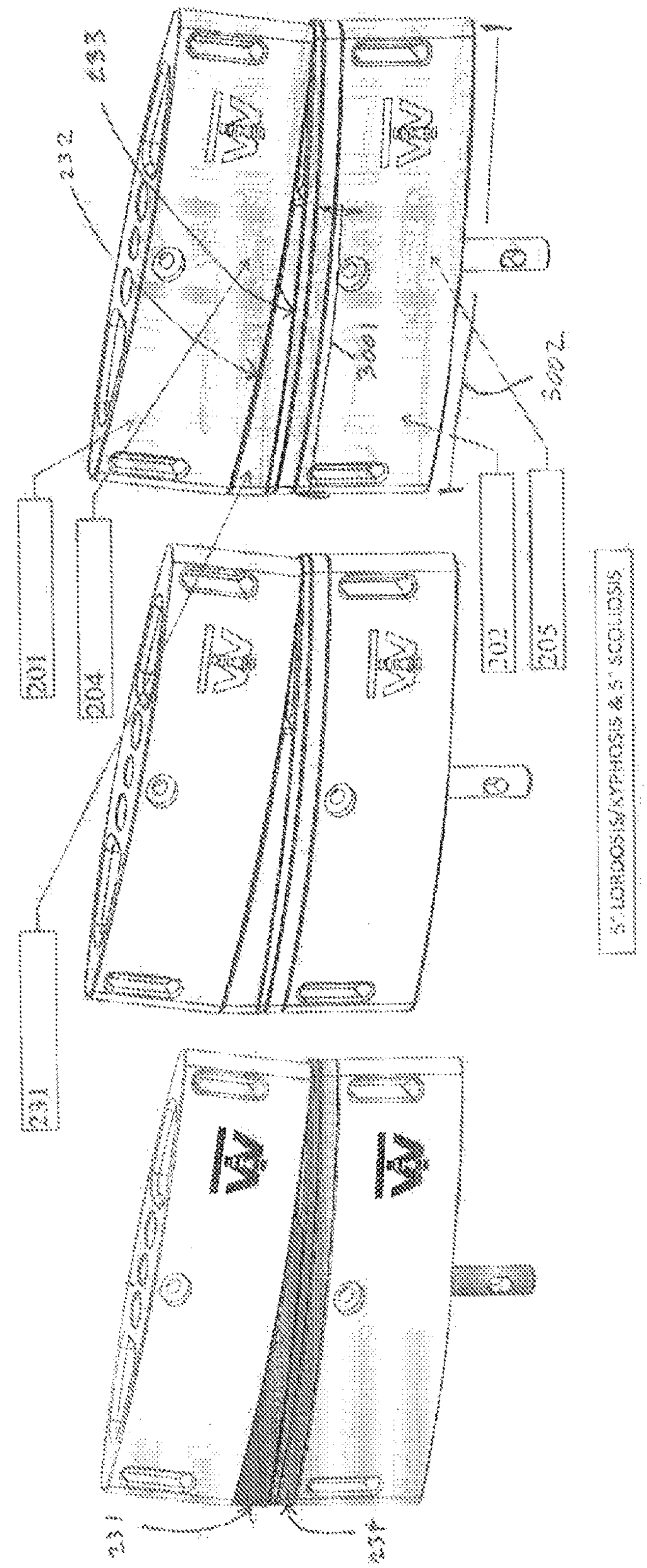
FIGS. 30A, 30B, 30C depict embodiments of subassemblies of modular wedge bushings.
Figure 32B:
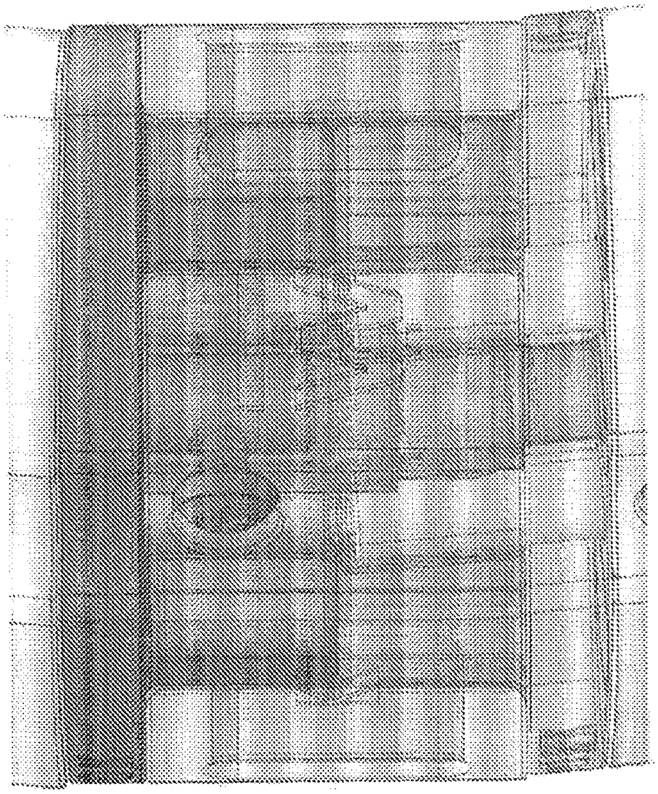
FIGS. 32A, 32B depict embodiments of a portion of a spinal support system.
Figure 32A:
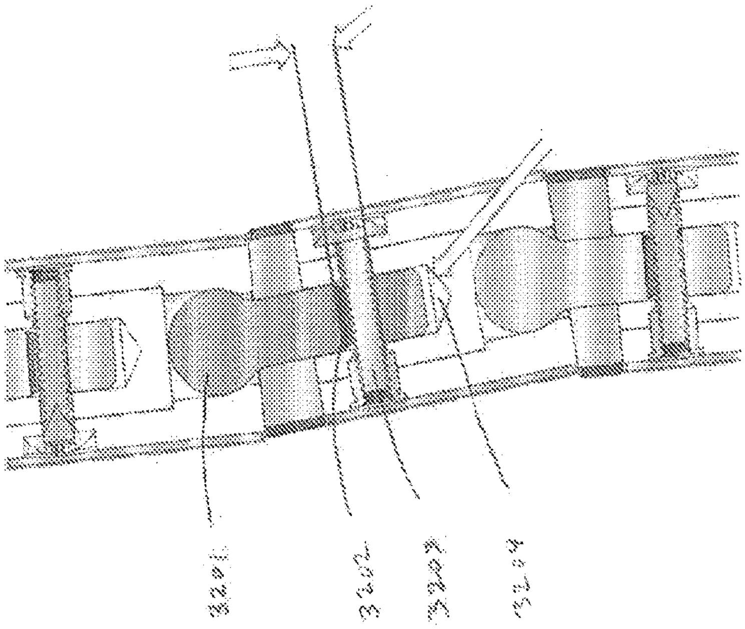
Figure 38A:
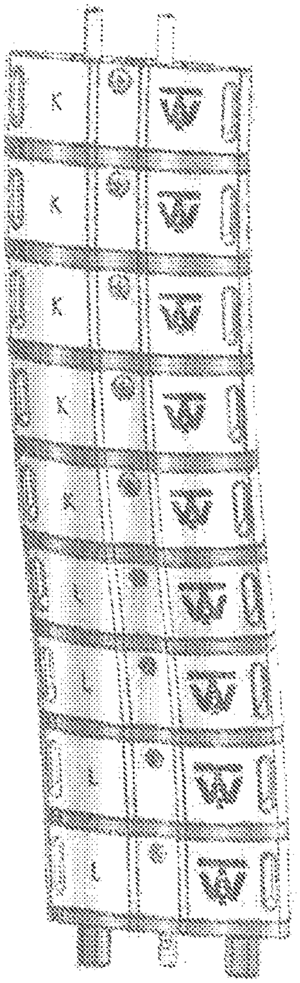
FIGS. 38A, 38B, 38C, 38D, 38E, 38F depict various views of an embodiment of a portion of a spinal support system.
Figure 38B:
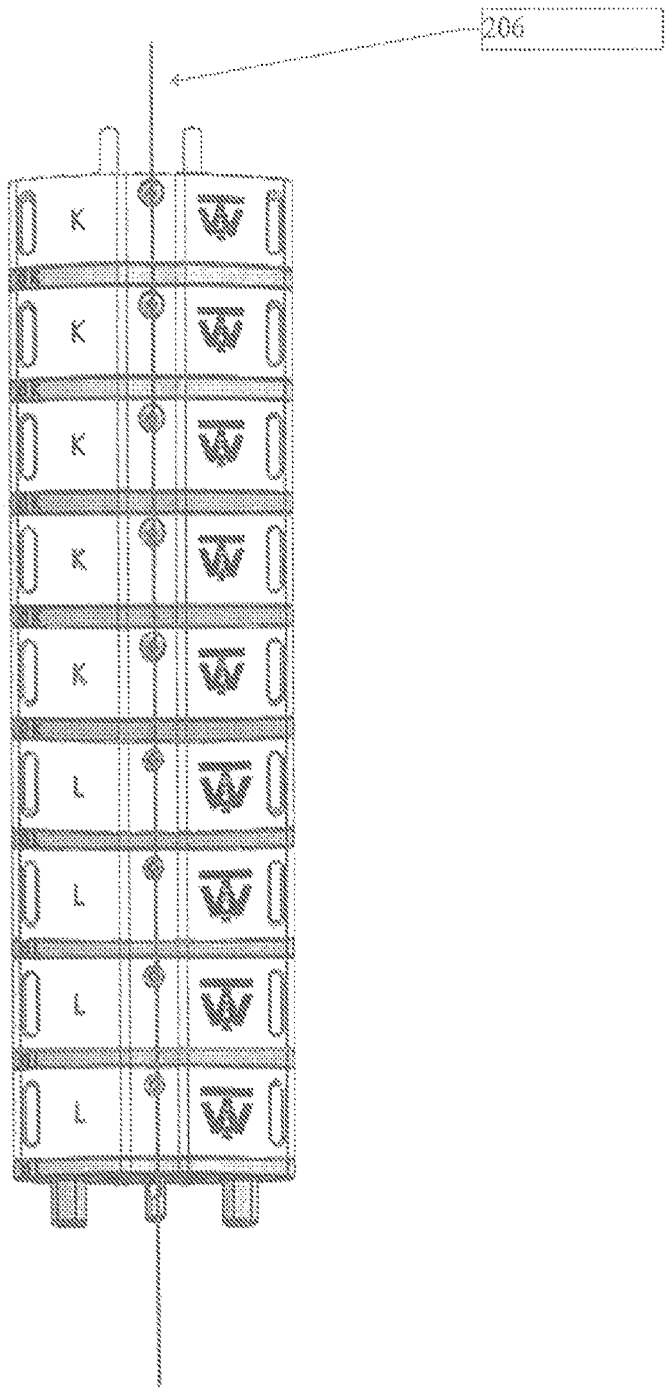
Figure 38C:
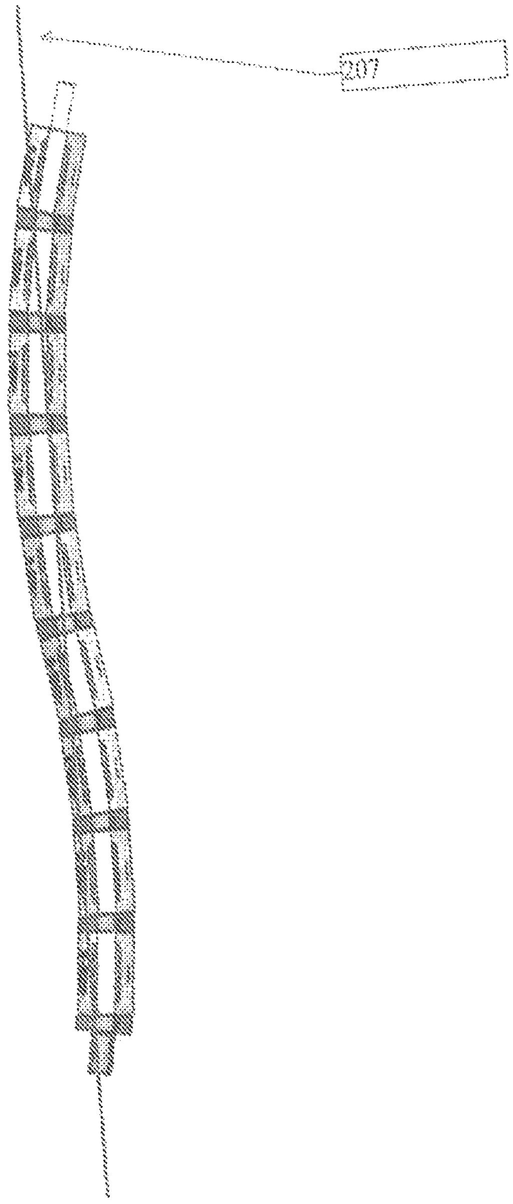
Figure 38D:
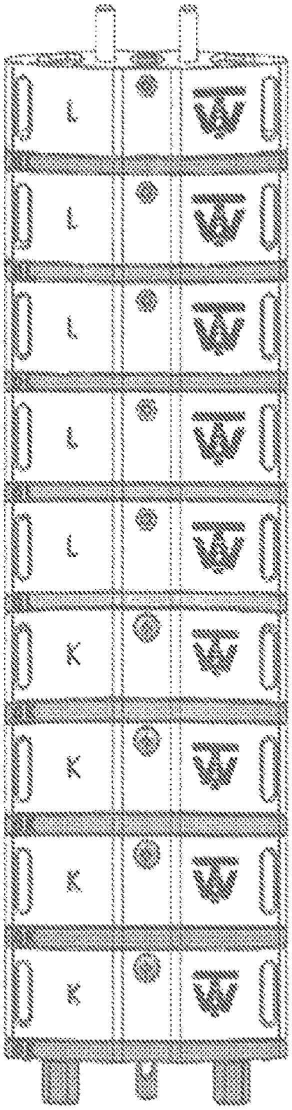
Figure 38E:
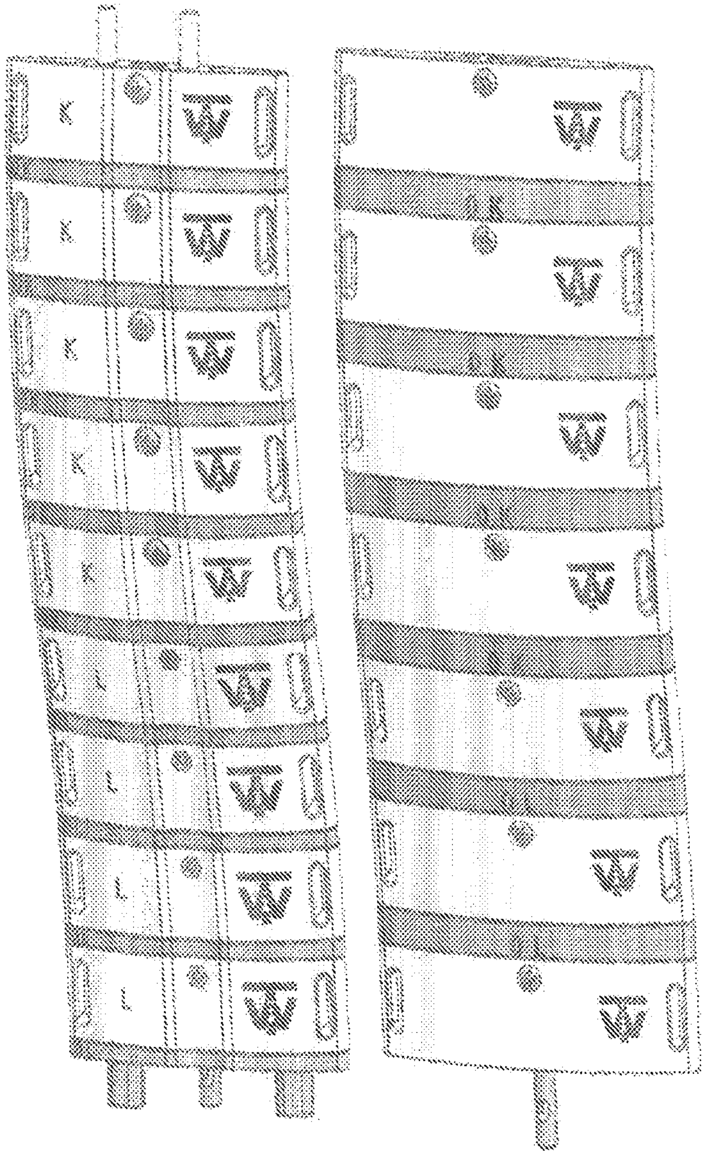
Figure 38F:
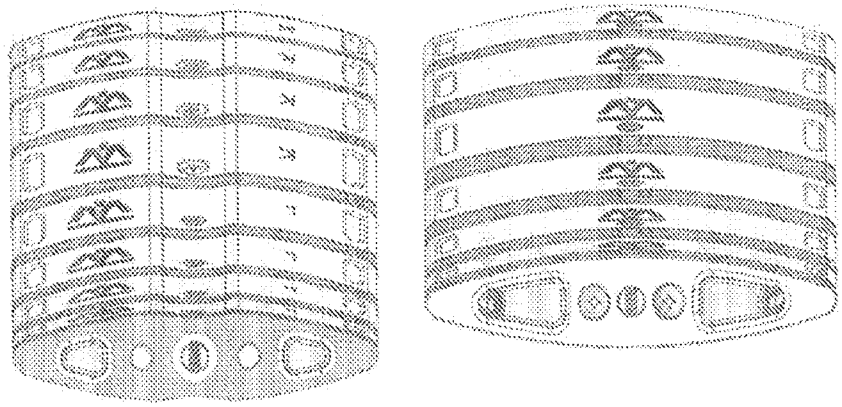

See, for example, FIG. 30(C). Joints 204, 205 are depicted in phantom and are similar to, in some embodiments, the ball and socket joints of FIGS. 12, 14B. FIG. 32(A) also depicts ball and socket joints. Coronal and sagittal planes are addressed in, for example, FIGS. 38(B) and 38(C).

As used herein, a bushing is a type of motion resistance resilient member. It provides an interface between two parts, supporting them in an initial relative position, creating stability and resisting motion in multiple planes by providing a reaction force to the movement.

Because the first plane of the first bushing is not parallel to the second plane of the first bushing, the bushing may impart scoliosis (i.e., a curvature) to the brace or a portion thereof. However, such a non-parallel orientation may instead impart a lordosis/kyphosis aspect to the brace or a portion thereof. Further still, such a non-parallel orientation may impart both scoliosis and lordosis/kyphosis to the brace.

Example 1.1b. The system according to example 1b, wherein the superior surface directly contacts the first vertebral segment.

See, for example, FIG. 30(C).

Example 1.2b. The system according to example 1.1b, wherein the inferior surface directly contacts the second vertebral segment.

Figure 28C:
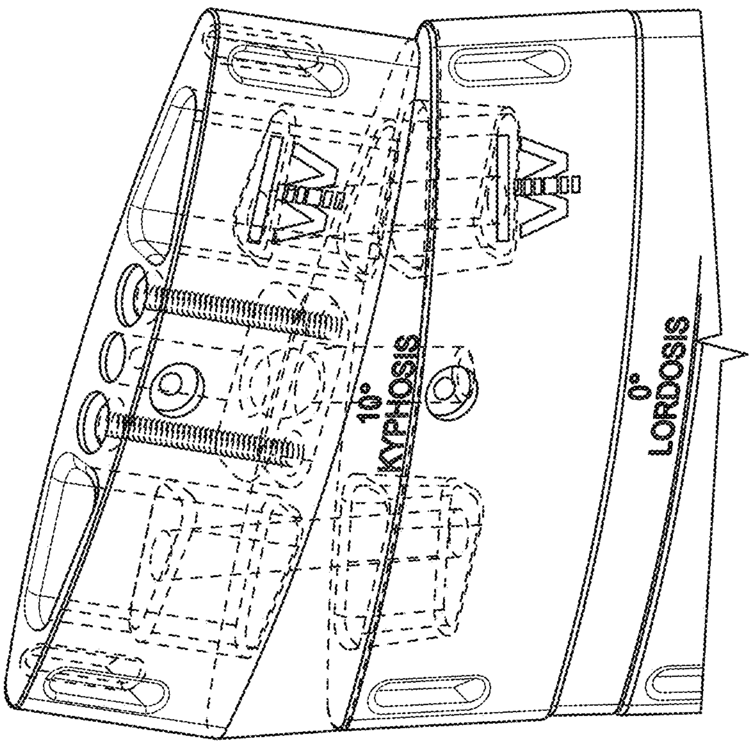
FIGS. 28A, 28B, 28C depict subassemblies of embodiments of bushings.
Figure 28B:
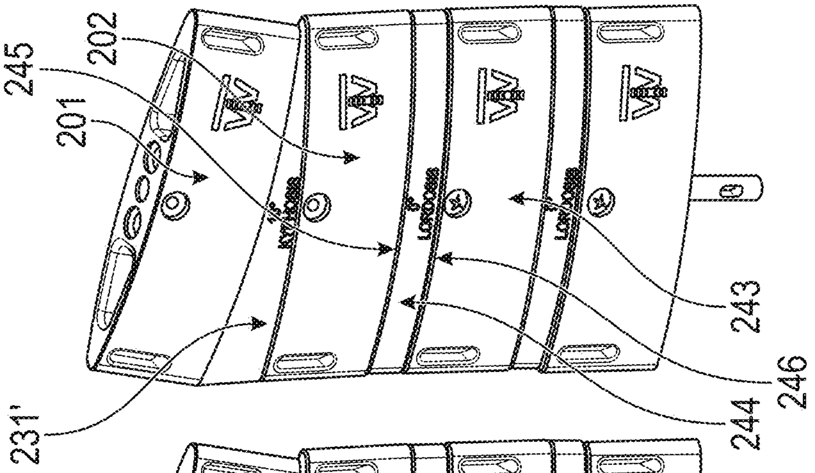
Figure 28A:
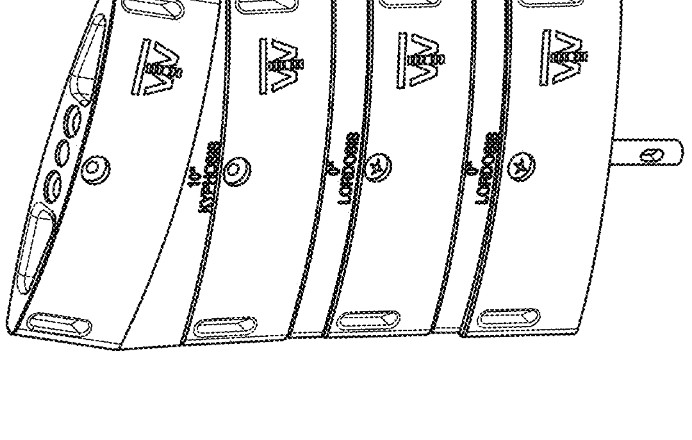

See, for example, FIG. 28(A). However, in other embodiments addressed herein, only one surface of the bushing may directly contact a vertebral segment. See, for example, FIG. 30(C). In other embodiments neither surface may directly contact a vertebral segment.

Example 1.3b. The system according to example 1b, wherein the inferior surface directly contacts the second vertebral segment.

Example 2b. The system according to any of examples 1b-1.1b comprising a sacral segment (103) that couples to the second vertebral segment via the second joint. The sacral segment includes first and second ratchets, the first ratchet comprising a first toothed rack (110) and a first spring-loaded finger (111) and the second ratchet comprising a second toothed rack (112) and a second spring-loaded finger (113). The first toothed rack includes a first outer surface (114) that is curved in the sagittal plane and the second toothed rack includes a second outer surface (115) that is curved in the sagittal plane.

Figure 11:
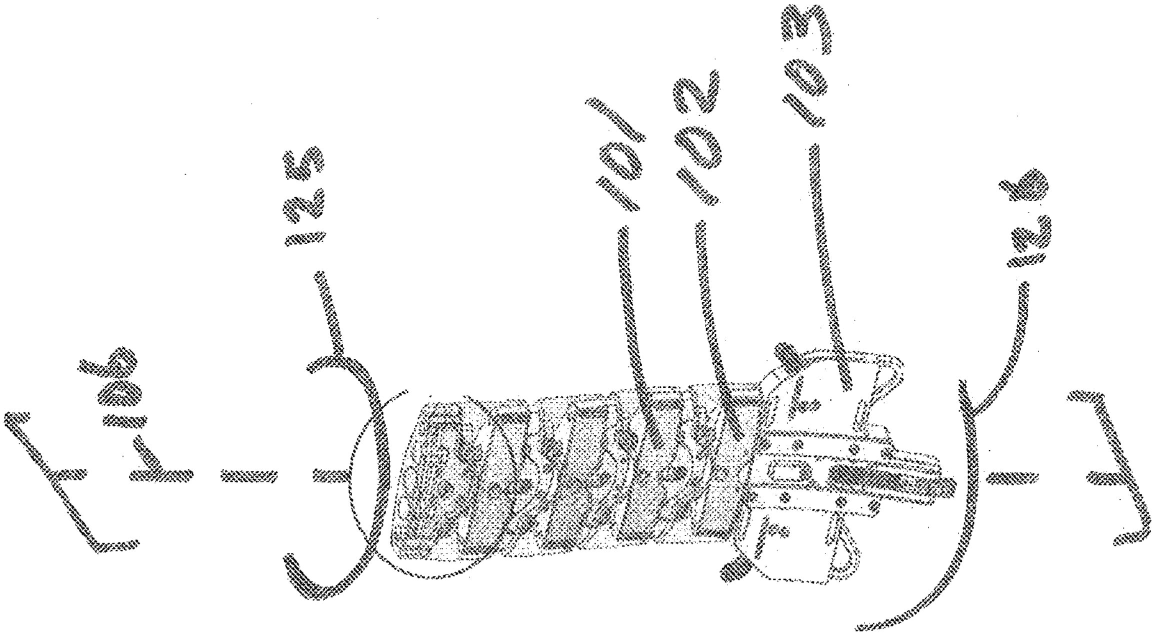
FIG. 11 depicts an embodiment of a spinal support system.
Figure 11:
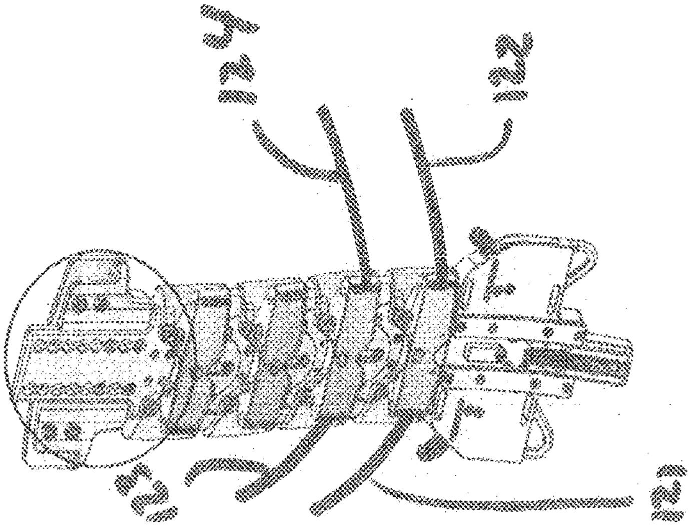
Figure 12:
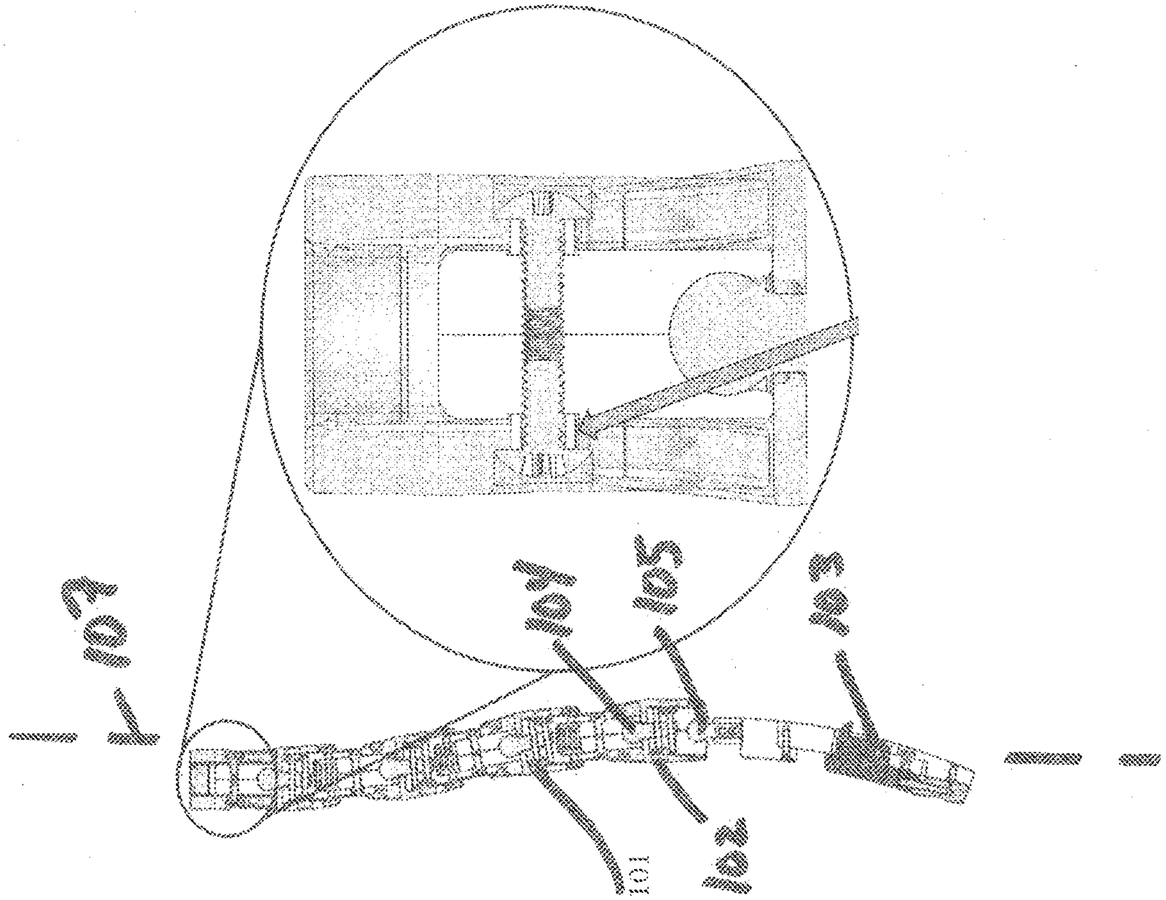
FIG. 12 depicts an embodiment of a portion of a spinal support system.
Figure 13:
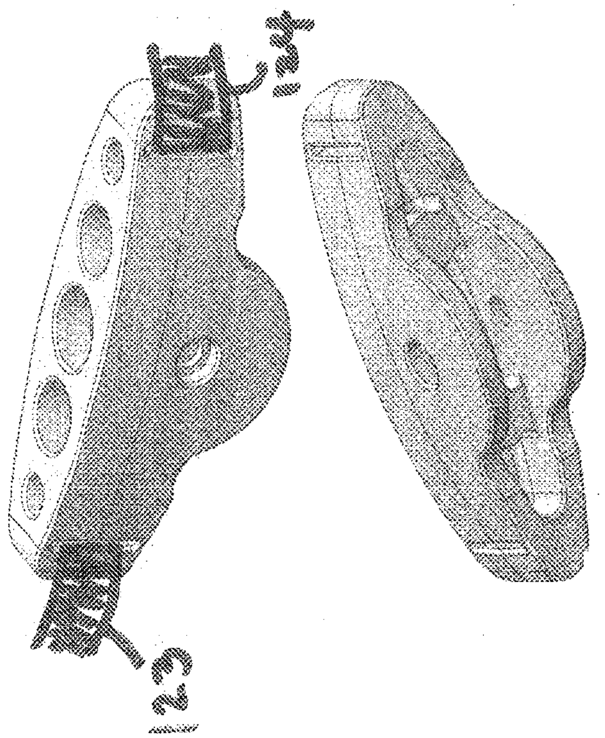
FIG. 13 depicts an embodiment of a portion of a spinal support system.
Figure 22A:
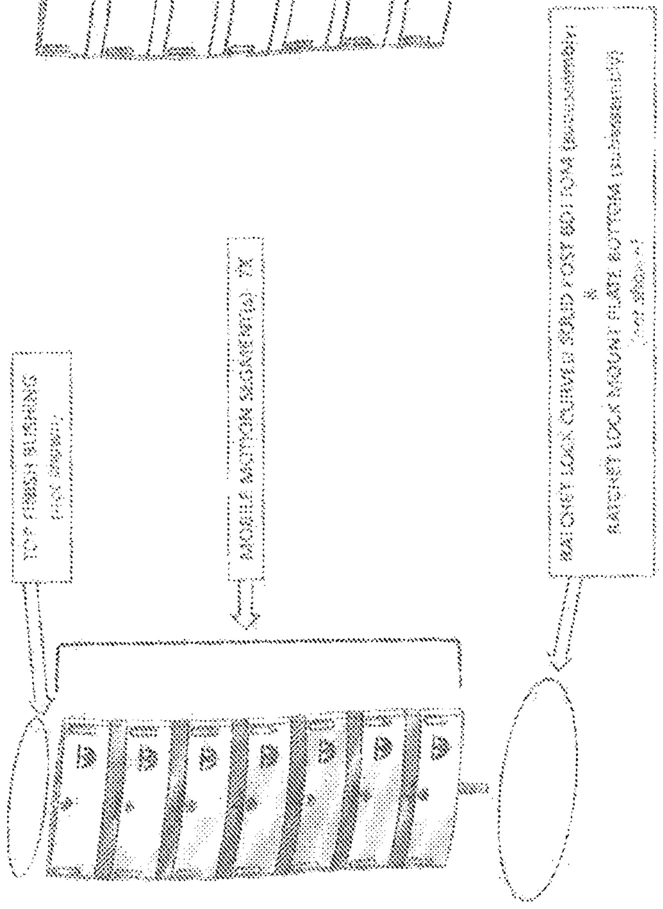
FIGS. 22A, 22B depicts an embodiment of a portion of a spinal support system with resilient bushings.
Figure 22B:
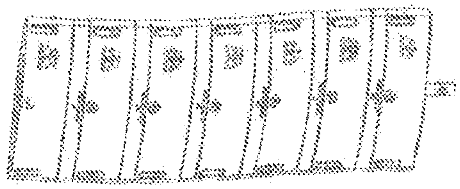
Figure 23:
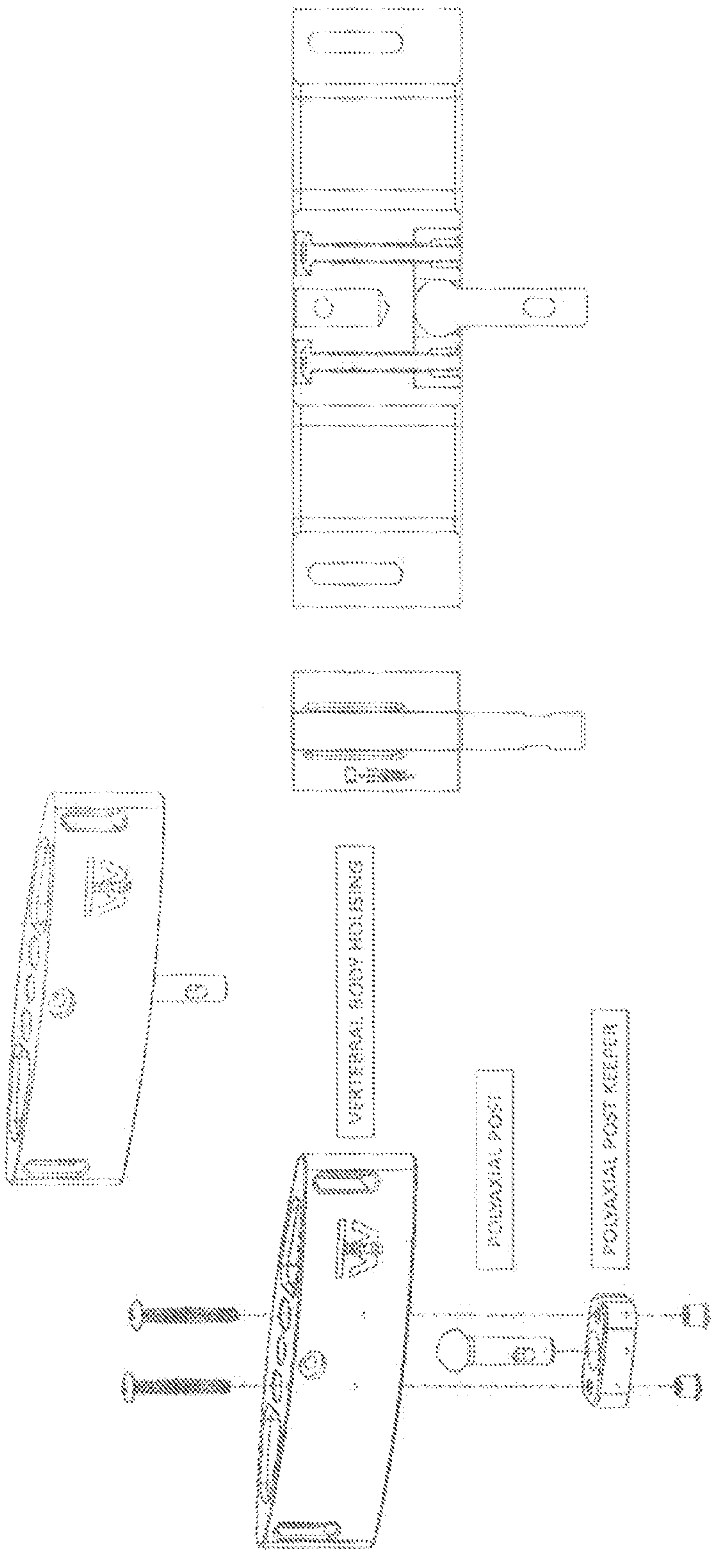
FIG. 23 includes an assembly perspective of a portion of a spinal support system.

Thus, in some embodiments the sacral segment of, for example, FIG. 11 may be coupled with a bushing-based embodiment such as the system of, for example, FIG. 22A.

Example 3b. The system of example 2b, wherein the first outer surface is rigid and non-malleable.

Example 4b. The system according to any of examples 1b-3b, wherein the second outer surface is rigid and non-malleable.

Example 5b. The system according to any examples 1b-4b, wherein the first outer surface has a first center of curvature (116) and at least a portion of the first tooth rack is between the first outer surface and the first center of curvature.

Example 6b. The system according to any of examples 1b-5b comprising a force sensor (117).

Example 7b. The system of example 6b, wherein the second joint is operatively coupled to the force sensor to convey force from the second joint to the force sensor.

Example 8b. The system of example 7b, wherein the second joint is slidingly coupled (FIG. 7) to the sacral segment.

Example 9b. The system of example 8b, wherein the second joint is not rigidly coupled to the force sensor or the sacral segment.

Example 10b. The system of example 9b, wherein the second joint has one of a male or female coupler (118, 119) and the sacral segment has another of the male or female coupler to slidingly and non-rigidly couple to the second joint's one of the male or female coupler.

Example 11b. The system of example 8b, wherein the first toothed rack includes a void (120) proportioned to receive the force sensor.

Example 12b. The system of example 8b, wherein the force sensor is included within the void.

Example 13b. The system according to any of examples 1b-12b, wherein the first toothed rack is slidingly coupled to the second toothed rack.

Example 14b. The system according to any of examples 1b-13b comprising: first opposing support members (121, 122) on opposing lateral sides of the first vertebral segment; and second opposing support members (123, 124) on opposing lateral sides of the second vertebral segment.

Another version of example 14b. The system according to any of examples 1b-13b comprising: a first number of support members (121, 123) on a first lateral side of the first vertebral segment; and a second number of support members (122) on a second lateral side of the first vertebral segment. The first and second lateral sides are on opposite sides of the first vertebral segment. The first number is unequal to the second number. A total number of support members are arranged asymmetrically to the first vertebral segment.

Example 14.1b A system according to any of examples 1b-14b, wherein the system is configured to provide a bending force to a patient's spine.

Example 14b.2. A system according to any of examples 1b-14b, wherein the system is configured to provide a torsional force to a patient's spine.

Example 14b.3. A system according to any of examples 1b-14b, wherein the system is configured to provide a torsional force to a patient's spine and a bending force to the patient's spine.

Example 15b. The system of example 14b comprising a top brace member (125) and a bottom brace member (126). The sacral segment and the first and second opposing support members are all between the top and bottom brace members.

Example 16b. The system of example 15b wherein the first ratchet is configured to increase the distance between the top and bottom brace members and consequently provide a distraction force to a user of the system.

Example 17b. The system of example 15b wherein the first ratchet is configured to increase the distance between the top and bottom brace members and consequently provide a posterior distraction force to a user of the system.

Example 18b. The system according to any of examples 1b-17b, wherein when the system is coupled to a user the sagittal plane intersects at least a portion of the user's spine.

Example 19b. The system according to any of examples 1b-18b, wherein the first toothed rack includes a void and the void includes at least a portion of the second spring-loaded finger.

Example 20b. The system according to any of examples 1b-18b, wherein the first toothed rack includes a void and the void includes at least a portion of at least one of the second spring-loaded finger and the second toothed rack.

Example 1c. The system according to any of examples 1b-1.1b comprising a sacral segment that couples to the second vertebral segment via the second joint. The sacral segment includes a first body (4101), a second body (4102) slidably coupled to the first body, and a cord (4103) slidably coupled to at least one of the first or second bodies.

Figures 41A, 41B, 41C:
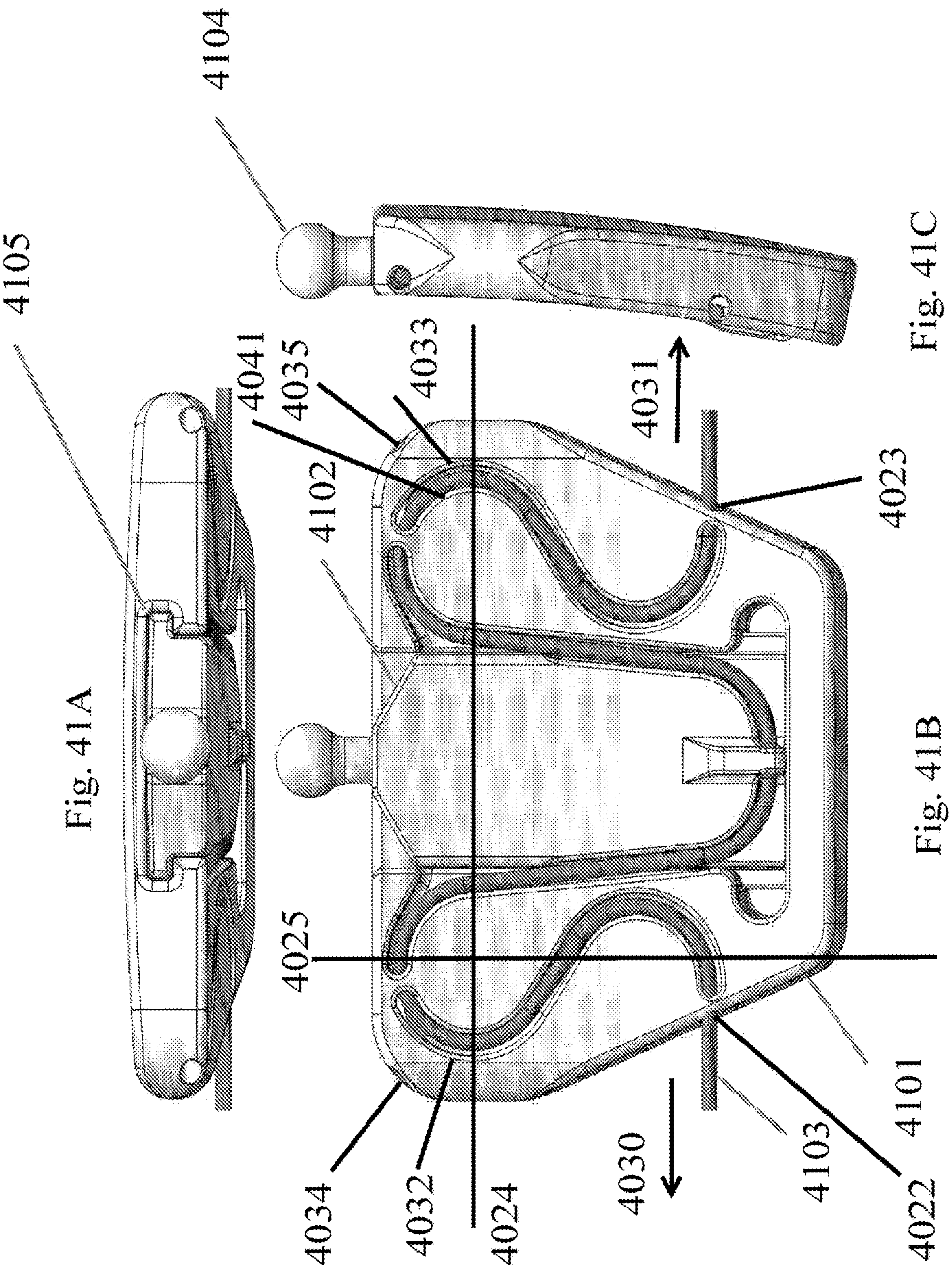
FIGS. 41A, 41B, 41C, 41D, 41E, 41F depict views of an embodiment of a cord and track-based system in the retracted state.
Figure 41D:
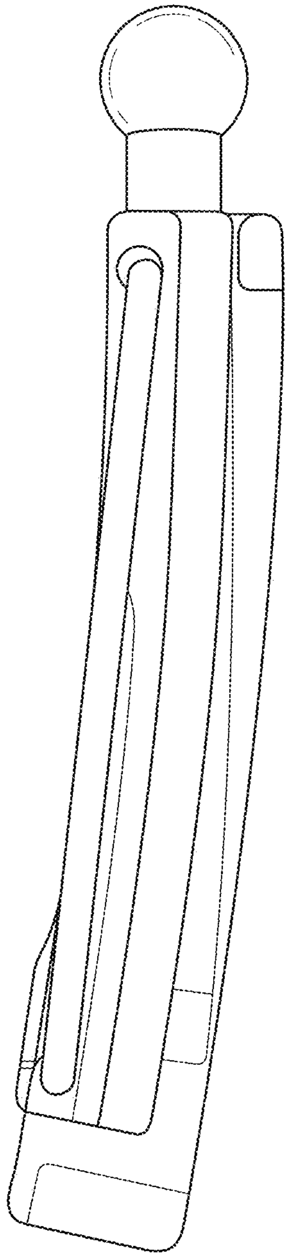
Figure 41E:
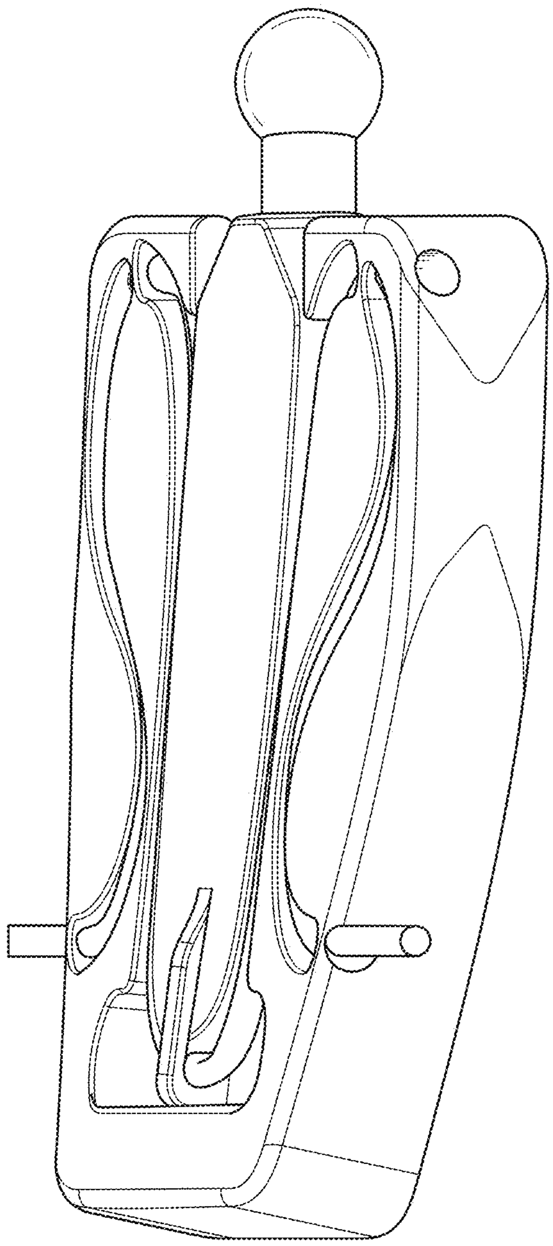
Figure 41F:
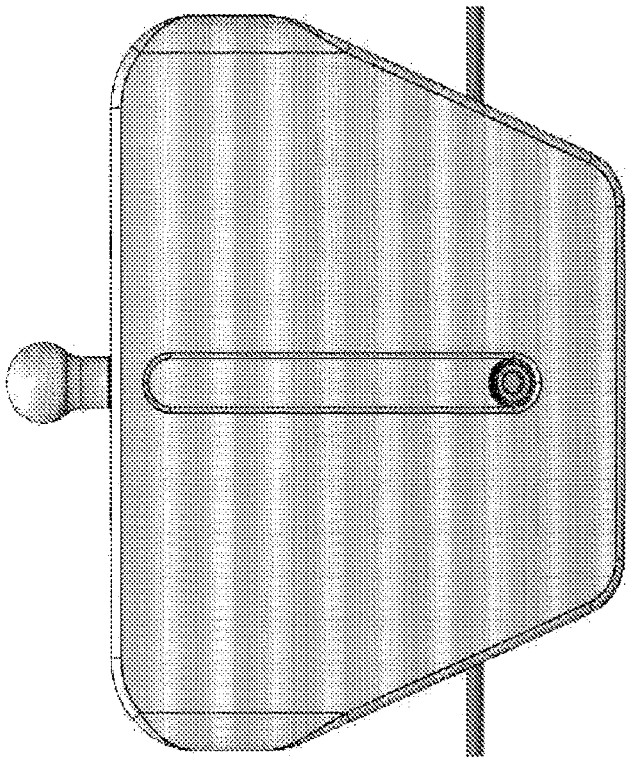
Figure 41I:
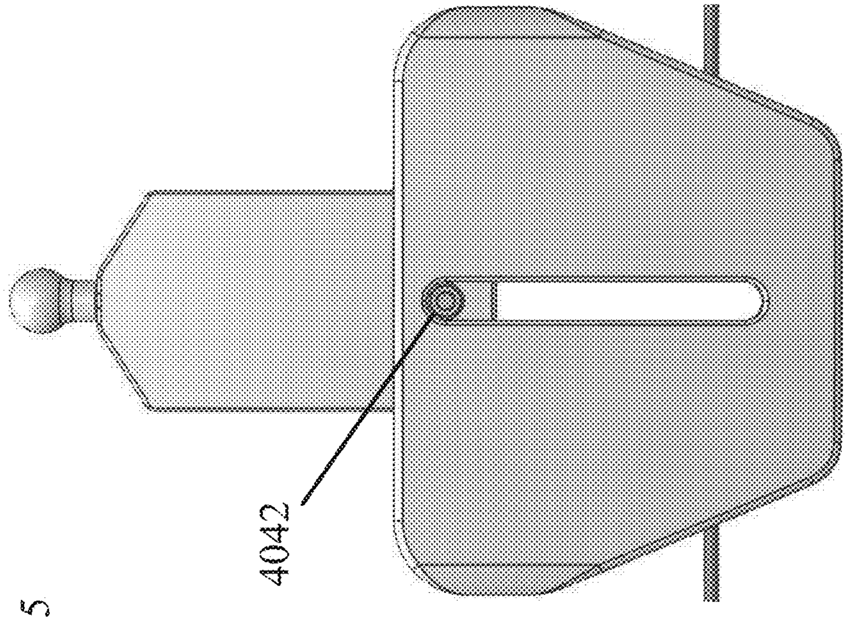
FIGS. 41G, 41H, 41I depict views of the embodiment in a deployed or non-retracted state.
Figure 41H:
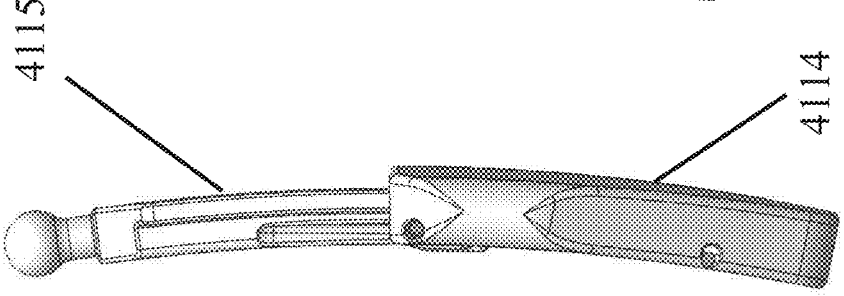
Figure 41G:
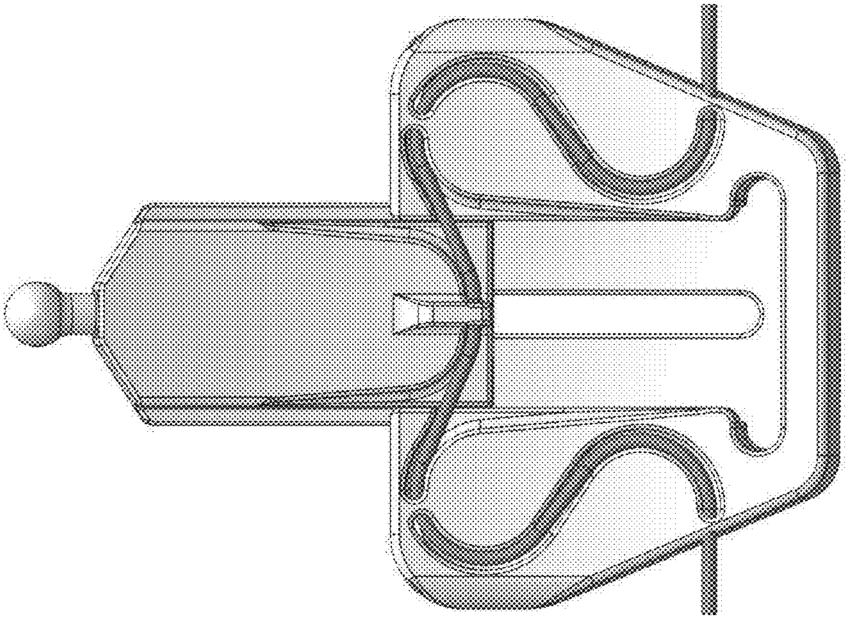

See, for example, FIGS. 41A-41C. The cord may be, for example, a stainless-steel wire cable coated in vinyl. The cable may be, for example, 1/16 inch thick.

Example 2c. The system of example 1c, wherein the cord is configured to slide the second body away from the first body when tension on the cord is increased.

For example, when the cord is pulled in one or both directions 4030, 4031, body 4102 is projected upwards to increase spinal distraction of the user.

Example 3c. The system according to any of examples 1c-2c, wherein the first body includes a slot (4105) and at least a portion of the second body is included in the slot.

The slot may be closed (like a tunnel) or open (at least at parts) as shown in FIG. 41B. The second body may be keyed to the slot via a projection, such as projection 4042.

Example 4c. The system according to any of examples 1c-3c, wherein the second joint has one of a male or female coupler (118, 119) and the sacral segment has another of the male or female coupler (4104) to couple to the second joint's one of the male or female coupler.

Example 5c. The system according to any of examples 1c-4c, wherein the first body includes a first outer surface (4114) that is curved in the sagittal plane and the second body includes a second outer surface (4115) that is curved in the sagittal plane.

Thus, in some embodiments the sacral segment of, for example, FIG. 41A may be coupled with a bushing-based embodiment such as the system of, for example, FIG. 22A.

The curvature helps the sacral segment better conform to the user's lower back.

Example 6c. The system of example 5c, wherein the first outer surface is rigid and non-malleable.

Example 7c. The system according to any of examples 5c-6c, wherein the second outer surface is rigid and non-malleable.

Example 8c. The system according to any examples 5c-7c, wherein the first outer surface has a first center of curvature and at least a portion of the second body is between the first outer surface and the first center of curvature.

Example 9c. The system according to any of examples 1c-8c comprising a force sensor.

Example 10c. The system of example 9c, wherein the second joint is operatively coupled to the force sensor to convey force from the second joint to the force sensor.

Example 11c. The system according to any of examples 1c-10c, wherein the second joint is slidingly coupled to the sacral segment.

Example 12c. The system of example 11c, wherein the second joint is not rigidly coupled to the force sensor or the sacral segment.

Example 13c. The system of example 9c, wherein the second body includes a void proportioned to receive the force sensor.

Example 14c. The system of example 13c, wherein the force sensor is included within the void.

Example 15c. The system according to any of examples 1c-14c comprising first opposing support members (121, 122) on opposing lateral sides of the first vertebral segment; and second opposing support members (123, 124) on opposing lateral sides of the second vertebral segment.

Another version of example 15c. The system according to any of examples 1c-14c comprising: a first number of support members (121, 123) on a first lateral side of the first vertebral segment; and a second number of support members (122) on a second lateral side of the first vertebral segment. The first and second lateral sides are on opposite sides of the first vertebral segment. The first number is unequal to the second number. A total number of support members are arranged asymmetrically to the first vertebral segment.

Example 16c. A system according to any of examples 1c-15c, wherein the system is configured to provide a bending force to a patient's spine.

Example 17c. The system according to any of examples 1c-16c, wherein the system is configured to provide a torsional force to a patient's spine.

Example 18c. The system of example 15c comprising a top brace member (125) and a bottom brace member (126), wherein the sacral segment and the first and second opposing support members are all between the top and bottom brace members.

Example 19c. The system of example 18c wherein the cord is configured to increase the distance between the top and bottom brace members and consequently provide a distraction force to a user of the system when tension on the cord is increased.

Example 20c. The system of example 19c wherein the distraction force is a posterior distraction force.

Example 21c. The system according to any of examples 1c-20c, wherein when the system is coupled to a user the sagittal plane intersects at least a portion of the user's spine.

Example 22c. The system according to any of examples 1c-20c comprising an arcuate channel (4021), wherein the cord is included in the arcuate channel.

See, for example, arcuate portions 4032, 4033.

Example 23c. The system according to any of examples 1c-22c, wherein the cord exits the sacral segment at a first location (4022).

Example 24c. The system of example 23c, wherein the cord exits the sacral segment at a second location (4023).

However, see also locations 4034, 4035. The cord may exit these locations instead of locations 4022, 4023 to vary the amount of force needed to be applied to the cord to move the second body.

Example 25c. The system according to any of examples 1c-24c comprising a first plane (4024) that is orthogonal to a second plane (4025), wherein the first plane intersects the cord at least 3 times.

Figure 39:
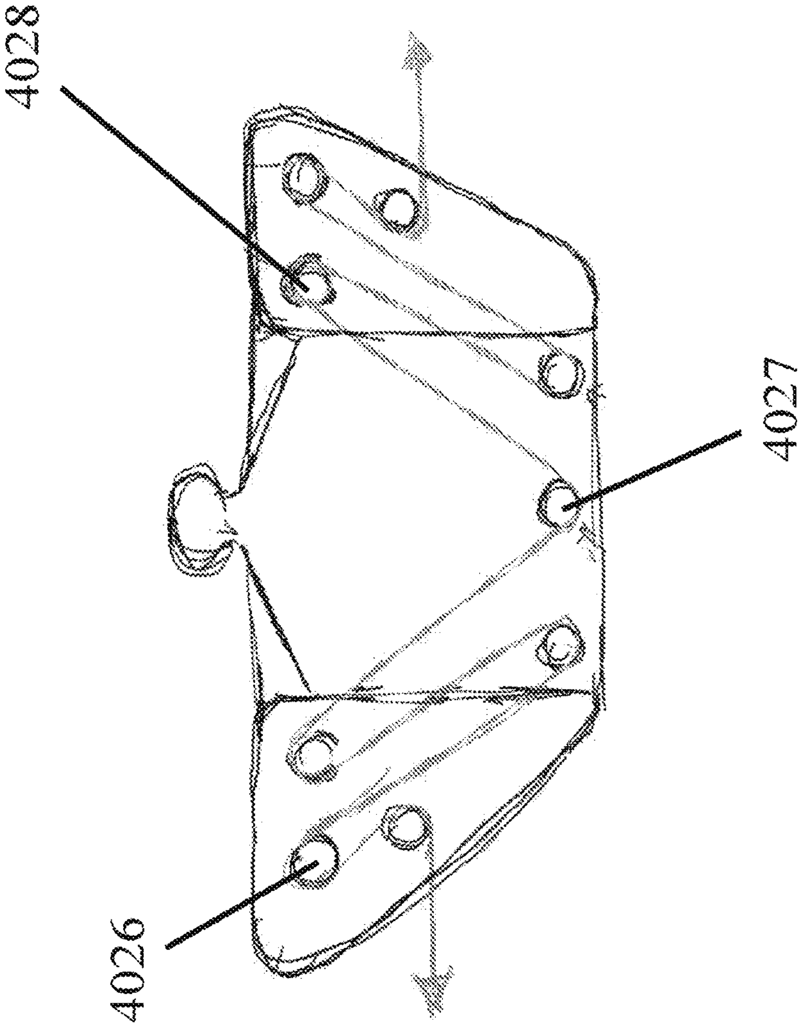
FIG. 39 depict an embodiment of a pulley-based distraction system.
Figure 42B:
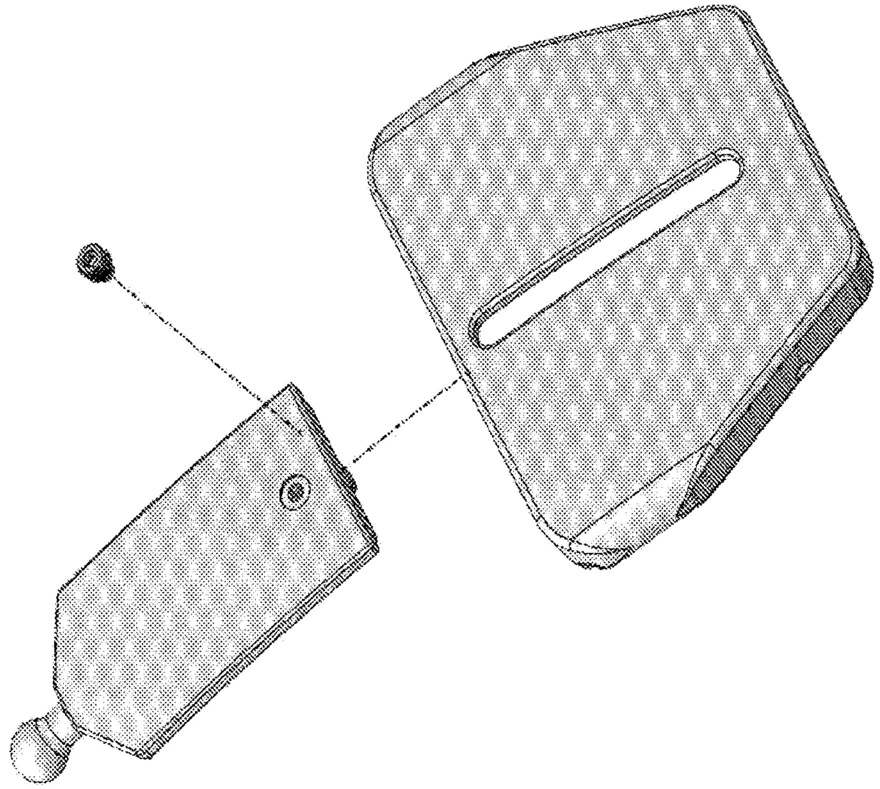
FIGS. 42A-42B depict exploded views of the embodiment of FIGS. 41A-41I.
Figure 42A:
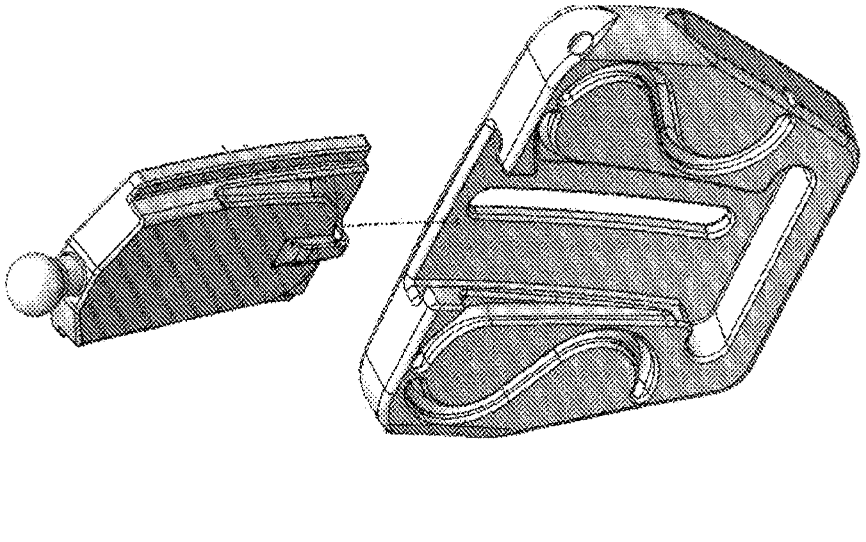

The arcuate path of the cord, as shown in FIG. 39 or 42A, provides a mechanical advantage to magnify any forced that increases tensions in the cord, such as when the cord is pulled in directions 4030 and/or 4031.

By positioning pivots points as shown in the embodiments (e.g., FIGS. 39, 41B), the pulley-like pivot points may provide a force reduction of, for example, 1/6. In an embodiment, a 6 inch pull on the cord may result in sliding the second body 2 inches upwards. While actual pulleys are not shown in the figures, other embodiments may include one or more pulleys. Further regarding the above-mentioned mechanical advantage, by locating the pivot points on upper and lower portions of the sacral element the force vector applied to the second body (due to increasing tension on the cord) is more vertical and hence, more efficient.

In an embodiment, the bend radius (e.g., bend radius 4041) may be configured to avoid binding of the cord. The radius may vary but may be, for example, 0.41 inches.

Example 26c. The system according to example 25c, wherein the first plane intersects the cord at least 4 times.

Example 27c. The system according to any of examples 25c-26c, wherein the second plane intersects the cord at least 2 times.

Example 28c. The system of example 27c, wherein the second plane intersects the cord at least 3 times.

Example 29c. The system according to any of examples 1c-28c, wherein lateral walls of the sacral segment taper medially as the lateral walls extend away from the first vertebral segment.

This tapering helps increase comfort for the user's lower back where the back interfaces the sacral element. Further, any reduction in material helps reduce the overall weight of the system, which also increases comfort for the user.

Example 30c. The system of example 1c comprising a first pivot point (4026), a second pivot point (4027), and a third pivot point (4028), wherein the cord wraps around a portion of the first pivot point, a portion of the second pivot point, and a portion of the third pivot point.

Figure 40C:
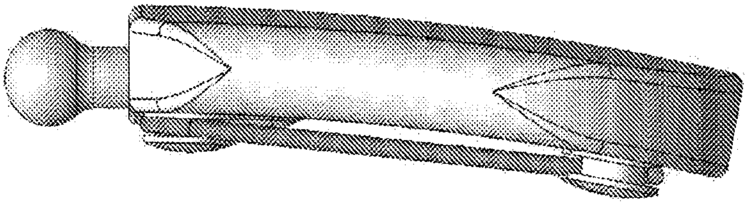
FIGS. 40A, 40B, 40C depict an embodiment of a pulley-based distraction system.
Figure 40A:
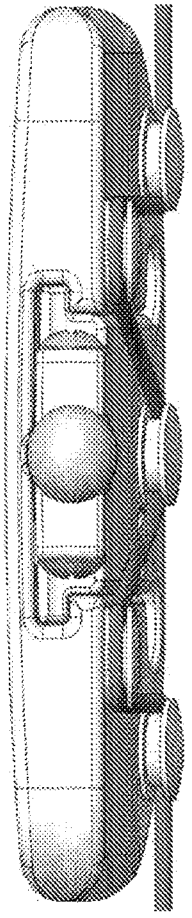
Figure 40B:
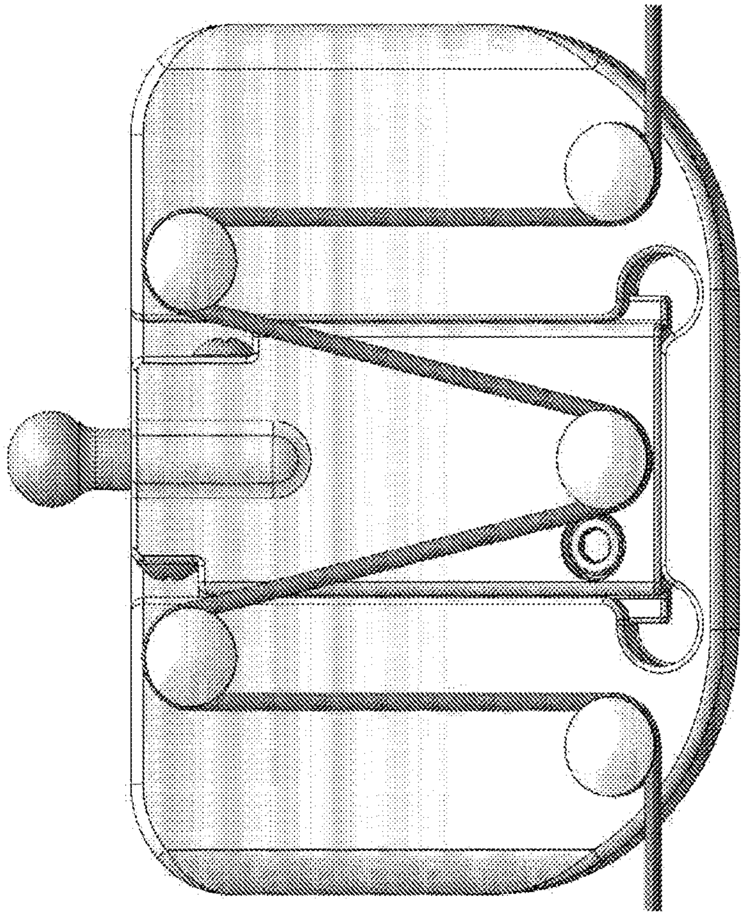

See, for example, FIGS. 39 and 40B.

Example 31c. The system of example 30c, wherein the first and third pivot points are included on the first body and the second pivot point is included on the second body.

Another version of example 1b. An external spinal brace system comprising: a first vertebral segment (101); a first joint (104); a second vertebral segment (102) that couples to the first vertebral segment via the first joint; a second joint (105); a sacral segment (103) that couples to the second vertebral segment via the second joint. A sagittal plane (106) intersects the first and second vertebral segments, the first and second joints, and the sacral segment. A coronal plane (107) intersects one or more of: (b)(i) the first and second vertebral segments, (b)(ii) the first and second joints, and (b)(iii) the sacral segment. The sacral segment includes first and second ratchets, the first ratchet comprising a first toothed rack (110) and a first spring-loaded finger (111) and the second ratchet comprising a second toothed rack (112) and a second spring-loaded finger (113). The first tooth rack includes a first outer surface (114) that is curved in the sagittal plane and the second tooth rack includes a second outer surface (115) that is curved in the sagittal plane.

Figure 24A:
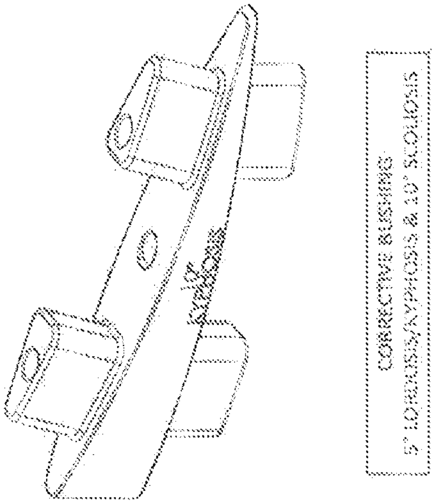
FIGS. 24A, 24B, 24C depict embodiments of corrective bushings.
Figure 24B:
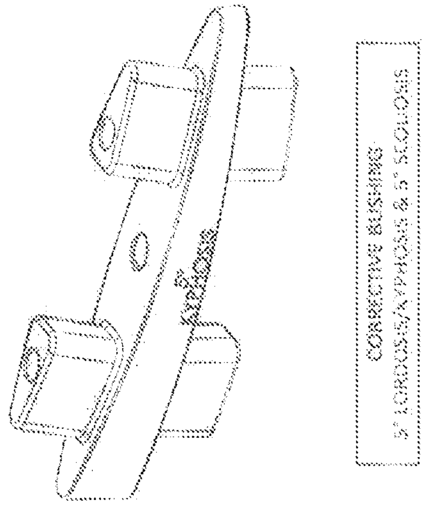
Figure 24C:
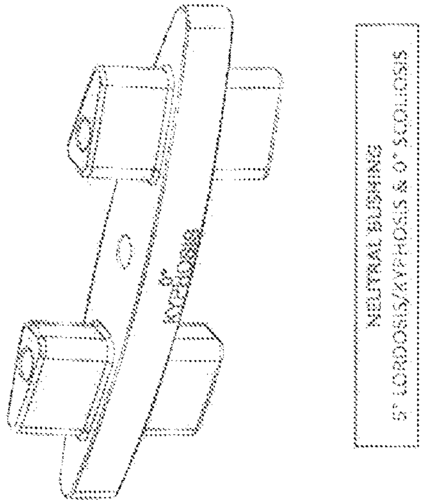

Another version of 1b. An external spinal brace system comprising: a first vertebral segment (201); a first joint (204); a second vertebral segment (202) that couples to the first vertebral segment via the first joint; a second joint (205); a bushing (231) between the first and second vertebral segments. A sagittal plane (206) intersects the first and second vertebral segments, the first and second joints, and the bushing. A coronal plane (207) intersects one or more of: (b)(i) the first and second vertebral segments, (b)(ii) the first and second joints, and (b)(iii) the bushing. The bushing includes a superior surface (232) disposed in a first plane of the first bushing and an inferior surface (233) disposed in a second plane of the first bushing, and the first plane of the first bushing is not parallel to the second plane of the first bushing. Such a superior surface is also shown in, for example, FIG. 24A. The inferior surface is not explicitly shown (at least not in its entirety) in FIG. 24A. Of course, in other embodiments the surface may not be entirely planar or even partially planar. For example, the surface may be knobbed or have some other pattern on it. Regardless, the bushing's surface (inferior and/or superior) may still provide a general angle of slope that imparts a desired force on the patient's spine.

Thus, in some embodiments not all joints are ball and socket joints but may instead be other joints (e.g., hinge) that provide varying degrees of freedom.

Example 21b. The system according to any of examples 1b-20b, comprising: a third vertebral segment (243) that couples to the second vertebral segment via the second joint; a second bushing (244) between the second and third vertebral segments. The second bushing includes a superior surface (245) disposed in a first plane of the second bushing and an inferior surface (246) disposed in a second plane of the second bushing. The first plane of the second bushing is parallel to the second plane of the second bushing.

For example, see FIG. 28B, which includes first bushing 231'. Because the first plane of the second bushing is parallel to the second plane of the second bushing, the second bushing imparts neither scoliosis nor lordosis/kyphosis. Still, the bushing may include a resilient material (e.g., rubber, polyurethane, silicone) that provides stability and general motion resistance.

Example 22b. The system according to any of examples 1b-20b, comprising: a third vertebral segment (243) that couples to the second vertebral segment via the second joint; a second bushing between the second and third vertebral segments. The second bushing includes a superior surface disposed in a first plane of the second bushing and an inferior surface disposed in a second plane of the second bushing. The first plane of the second bushing is not parallel to the second plane of the second bushing.

While in some embodiments the second bushing imparts neither scoliosis nor lordosis/kyphosis, in other embodiments the second bushing imparts scoliosis and/or lordosis/kyphosis in addition to any scoliosis and/or lordosis/kyphosis imparted by the first bushing.

Example 23b. The system according to any of examples 21b to 22b, wherein the first plane of the first bushing is not parallel to the first plane of the second bushing.

Thus, embodiments may include bushings having different degrees of angle, which when combined can impart lordosis/kyphosis and/or scoliosis to the brace and subsequently the patient. For example, see the bushings of FIGS. 25A and 25B.

Example 24b. The system according to example 23b, wherein: the first plane of the first bushing has a first degree of angle in the coronal plane; the first plane of the second bushing has a second degree of angle in the coronal plane; the first degree of angle in the coronal plane is unequal to the second degree of angle in the coronal plane.

Example 24.1b. The system according to example 23b, wherein: the first bushing is configured to impart a first degree of scoliosis; the second bushing is configured to impart a second degree of scoliosis; the first and second degrees of scoliosis are unequal to each other.

In some embodiments corresponding angles of the first and second bushings may be different or they may be the same. For example, a configuration may have consecutive bushings that have 5 degrees of scoliosis. That configuration may also have consecutive bushings that have 5 degrees of lordosis. In an embodiment the first degree of angle may be equal to the second degree of angle and the first and second degrees of scoliosis may be equal to each other. This also applies to embodiments that address lordosis/kyphosis.

Example 25b. The system according to any of examples 23b-24.1b, wherein: the first plane of the first bushing has a first degree of angle in the sagittal plane; the first plane of the second bushing has a second degree of angle in the sagittal plane; the first degree of angle in the sagittal plane is unequal to the second degree of angle in the sagittal plane.

Example 25.1b. The system according to any of examples 23b-24.1b, wherein: the first bushing is configured to impart a first degree of lordosis; the second bushing is configured to impart a second degree of lordosis; the first degree of lordosis is unequal to the second degree of lordosis.

At many locations herein, the term "lordosis/kyphosis" is used to indicate a degree of tilt in the sagittal plane, regardless of whether the brace is oriented to provide lordosis or kyphosis. At many locations herein, the term "scoliosis" is used to indicate a degree of tilt in the coronal plane, regardless of whether the brace is oriented to provide scoliosis.

Example 26b. The system according to any of examples 23b-24b, wherein: the first plane of the first bushing has a first degree of angle in the sagittal plane; the first plane of the second bushing has a second degree of angle in the sagittal plane; the first degree of kyphosis is unequal to the second degree of angle in the sagittal plane.

Figures 25A, 25B, 25C:
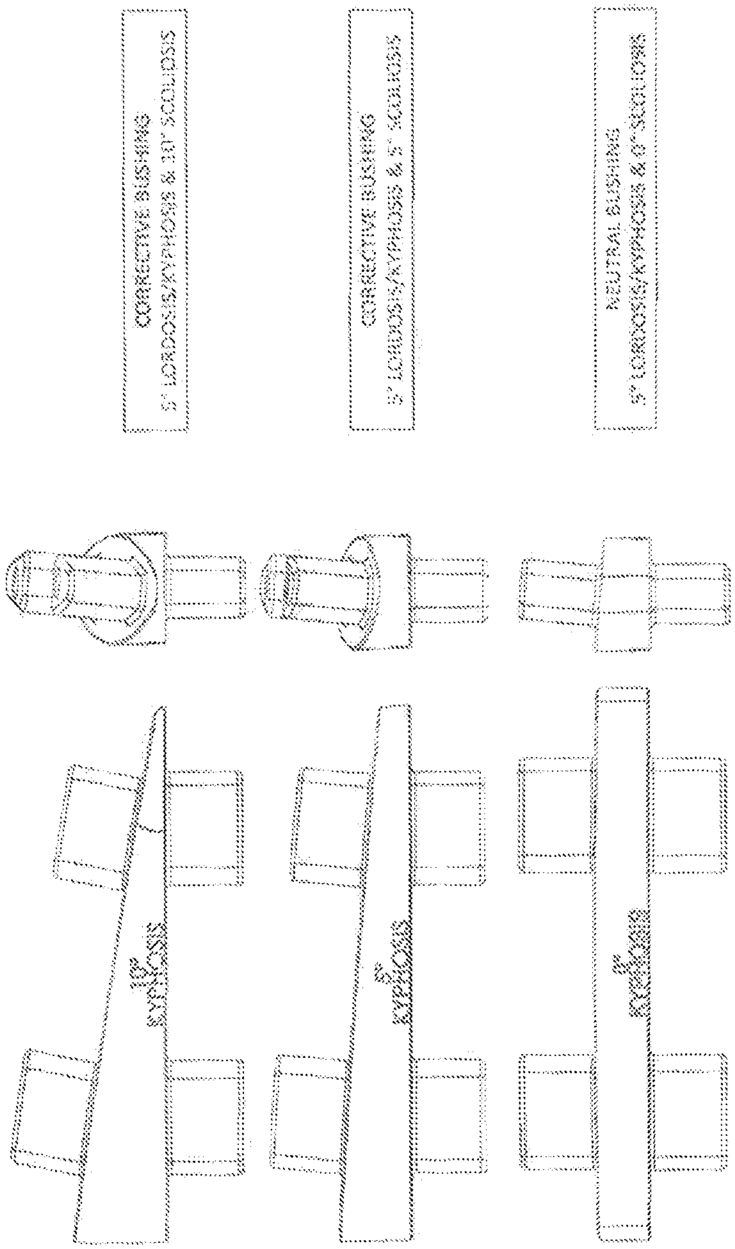
FIGS. 25A, 25B, 25C depict embodiments of corrective bushings.
Figure 26:
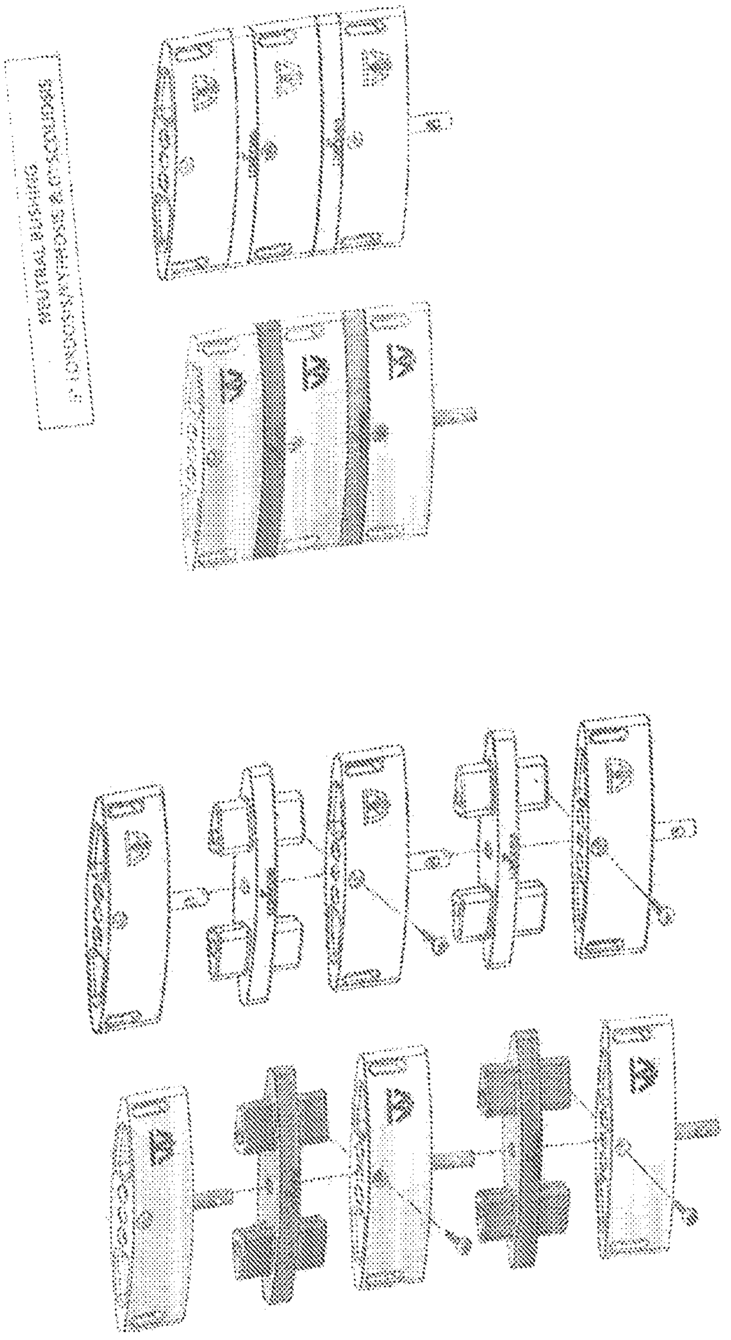
FIG. 26 depicts subassemblies of embodiments of bushings.
Figure 27C:
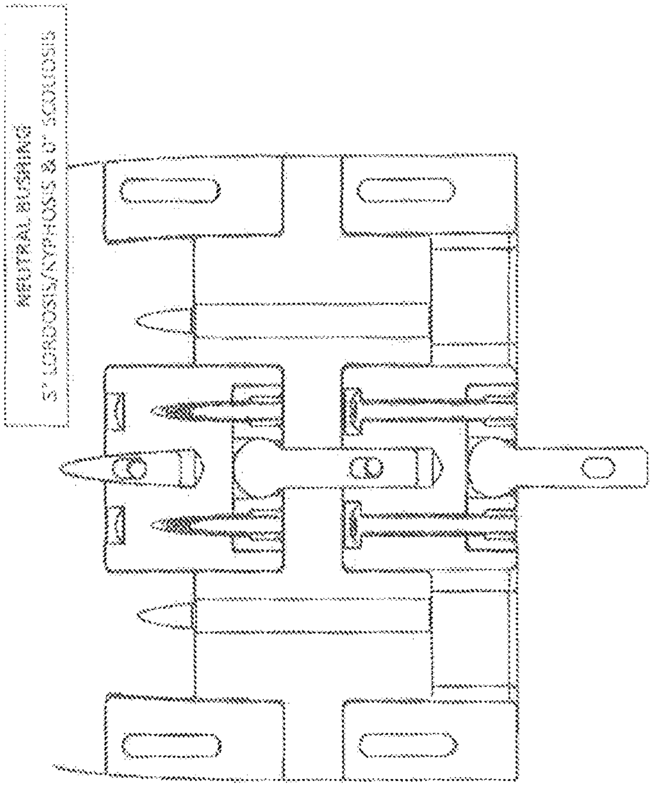
FIGS. 27A, 27B, 27C depict subassemblies of embodiments of bushings.
Figure 27B:
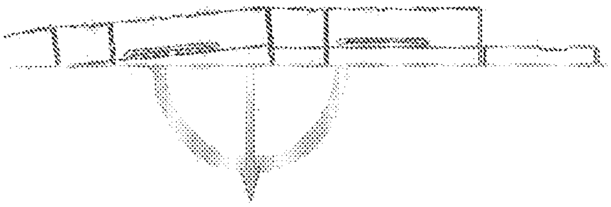
Figure 27A:
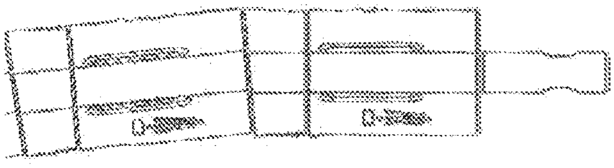

As used herein, kyphosis is described as a positive angle in the sagittal plane and lordosis is described as a negative angle in the sagittal plane For example, FIG. 25(A)-(C) show bushings that include varying combinations of scoliosis and lordosis/kyphosis inducement. For example, FIG. 25(C) shows zero scoliosis induced but 5 degrees lordosis/kyphosis induced whereas FIG. 25(A) shows both scoliosis and lordosis/kyphosis inducing angles.

Example 26.1b. The system according to any of examples 23b-24b, wherein: the first bushing is configured to impart a first degree of kyphosis; the second bushing is configured to impart a second degree of kyphosis; the first degree of kyphosis is unequal to the second degree of kyphosis.

Example 27b. The system according to any of examples 1b-26b, wherein the first bushing includes first (2901), second (2902), third (2903), and fourth (2904) projections. The first vertebral segment includes first and second voids and the second vertebral segment includes first and second voids. The first projection is included in the first void of the first vertebral segment and the second projection is included in the second void of the first vertebral segment. The third projection is included in the first void of the second vertebral segment and the fourth projection is included in the second void of the second vertebral segment.

Figure 29A:
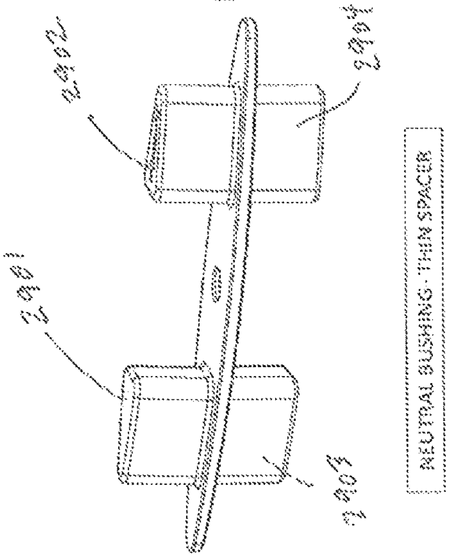
FIGS. 29A, 29B, 29C depict embodiments of modular wedge bushings.
Figure 29B:
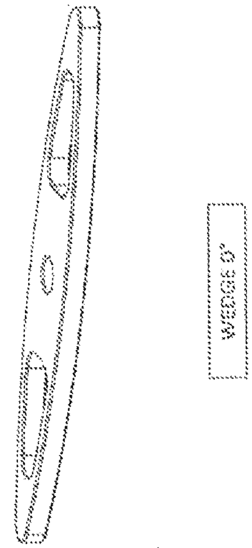
Figure 29C:
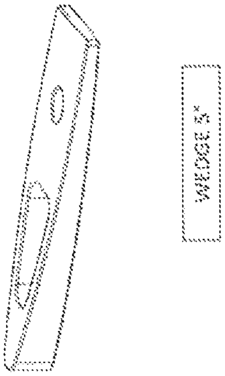
Figure 37:
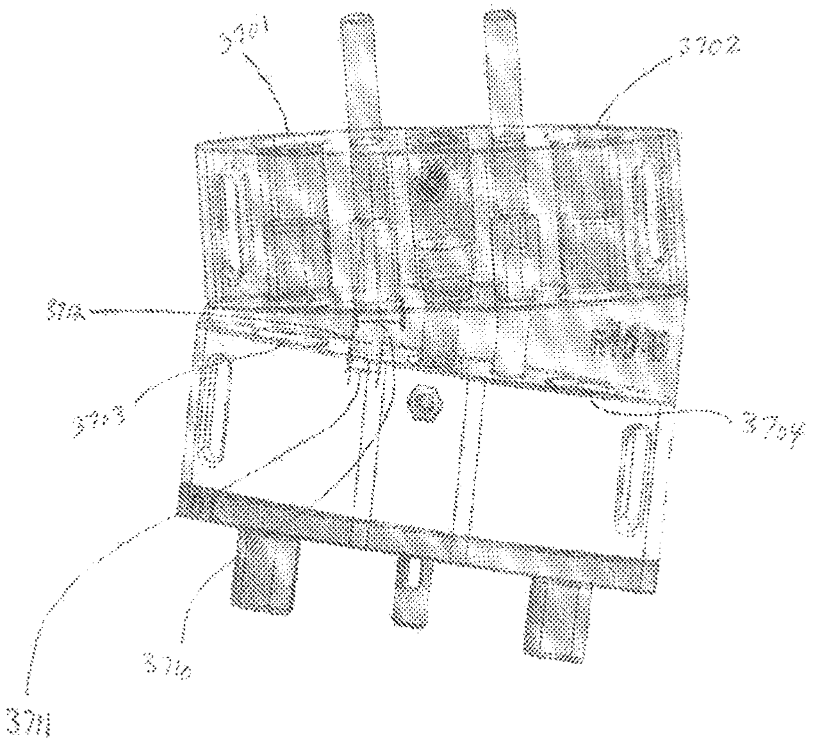
FIG. 37 depicts an embodiment of a portion of a spinal support system.

See, for example, FIG. 29A regarding the projections and FIG. 37 regarding the voids. For example, voids 3701, 3702, 3703, 3704 are configured to receive bushing projections. Other embodiments may include one, two, three, five or more projections to similarly couple a bushing to a vertebral segment. Similarly, the bushing may instead include voids to receive anchoring projection(s) from an adjacent vertebral segment.

Other coupling mechanisms are envisioned such as other male/female coupler arrangements to couple bushings to vertebral segments. Embodiments addressed herein allow for compression/decompression and for a modular system whose components may be exchanged with each other to provide various configurations of scoliosis and/or lordosis/kyphosis.

Example 28b. The system according to any of examples 1b-27b, wherein: the first bushing includes an aperture that couples the superior surface of the first bushing to the inferior surface of the first bushing. The aperture has a first maximum width where the aperture interfaces the superior surface of the first bushing. The aperture has a second maximum width where the aperture interfaces the inferior surface of the first bushing. The first maximum width is greater than the second maximum width.

Another version of 28b. The system according to any of examples 1b-27b, wherein: the first vertebral segment has an inferior surface that includes a first aperture. The second vertebral segment has a superior surface that includes a second aperture. The first aperture has a first maximum width (3710) where the first aperture interfaces the inferior surface of the first vertebral segment. The second aperture has a second maximum width (3711) where the second aperture interfaces the superior surface of the second bushing. the first maximum width is greater than the second maximum width.

Thus, in an embodiment the aperture in the bushing (that includes a rod that couples to the first and second apertures) may or may not have the same dimensions at its top and bottom.

For example, see FIG. 37. The unequal widths allow for a rod to mate with bushings having varying degrees of scoliosis (i.e., tilt in the coronal plane) between them while allowing for unresisted motion in the coronal plane (lateral bending) and resisting bending in the sagittal plane (flexion/extension) and torsion (rotation) in the axial plane.

Example 29b. The system according to example 28b comprising a rod (3712). The first vertebral segment includes an aperture. The second vertebral segment includes an aperture. The rod is included in the aperture of the first vertebral segment, the aperture of the second vertebral segment, and the aperture of the first bushing.

For example, see FIG. 37 wherein the rod provides stability to the system (e.g., prevents buckling), increases torsional resistance, increases bending resistance in the sagittal plane but not in the coronal plane, and does not affect the scoliosis and/or lordosis/kyphosis intended by one or more bushings. Because width 3710 (width of aperture on inferior side of first vertebral segment) is greater than width 3711 (width of aperture on superior side of second vertebral segment), rod 3712 still mates with the first vertebral segment despite the scoliosis of the bushing. In various embodiments one or more such rods or supporting members may be used to stabilize the brace systems.

Figure 33B:
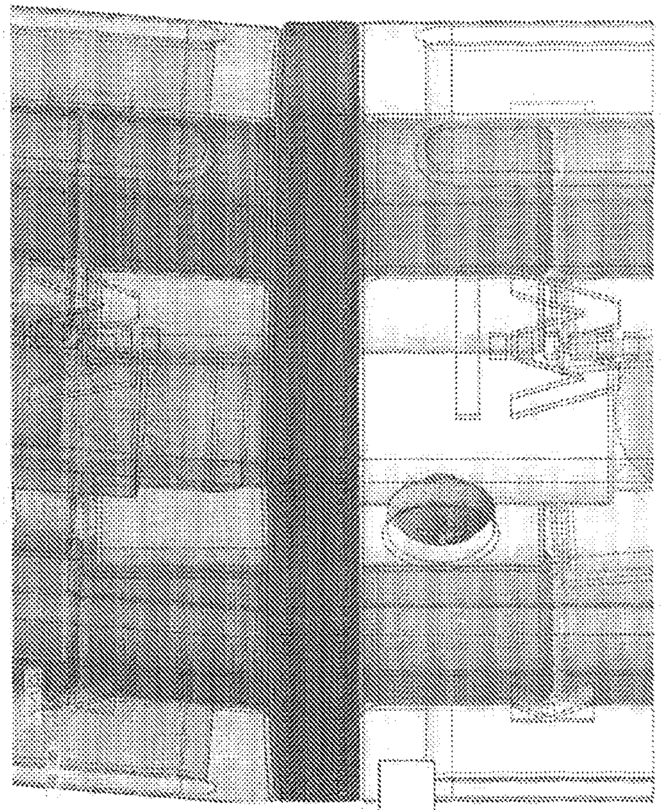
FIGS. 33A, 33B depict embodiments of a portion of a spinal support system.
Figure 33A:
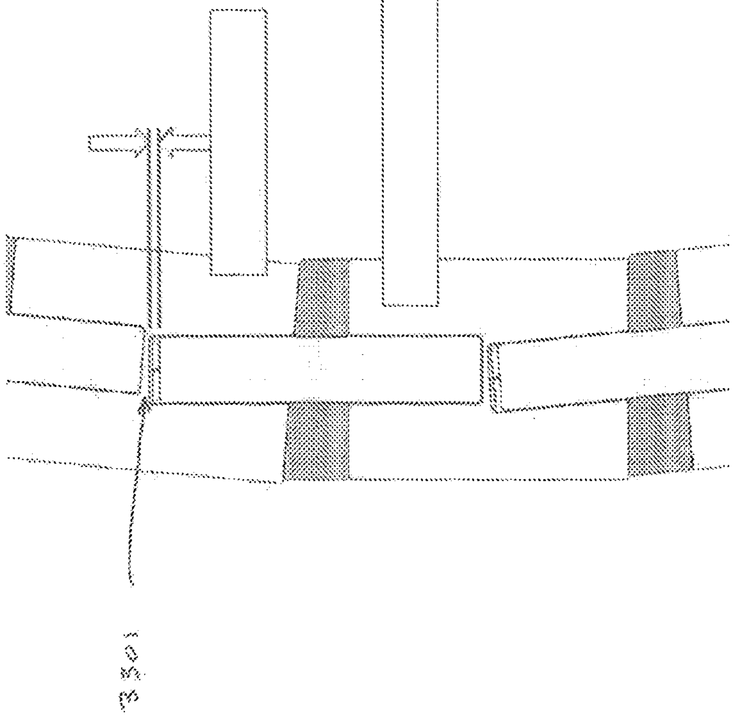
Figure 34A:
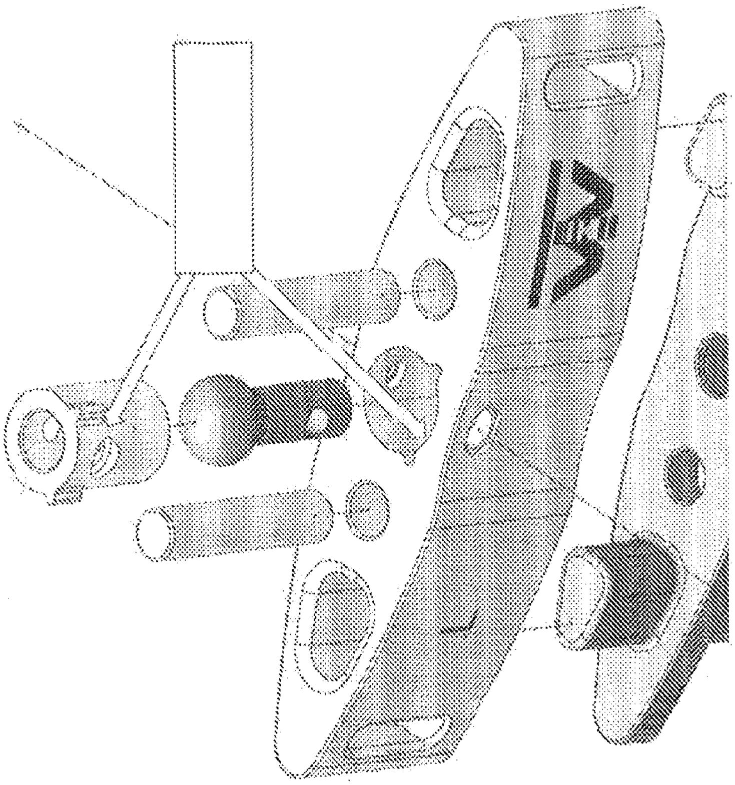
FIGS. 34A, 34B depict embodiments of a portion of a spinal support system.
Figure 34B:
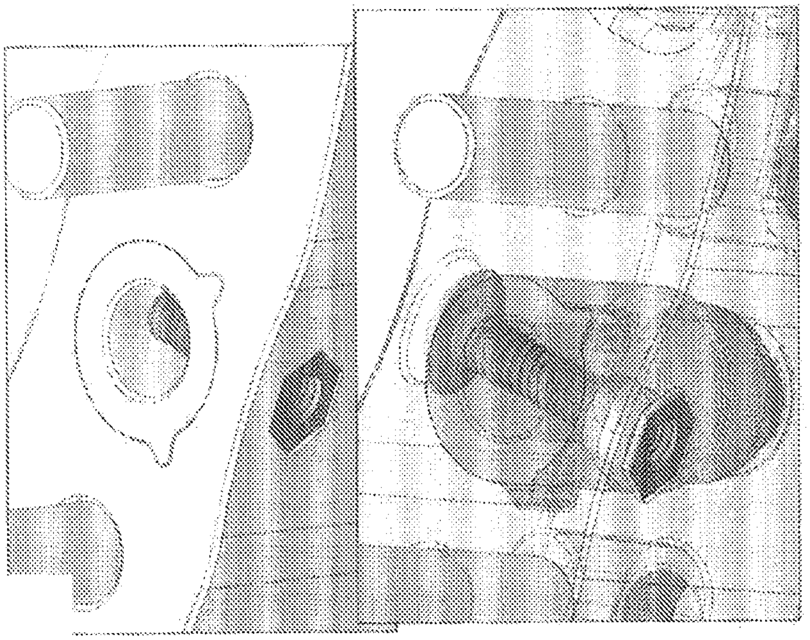
Figure 35:
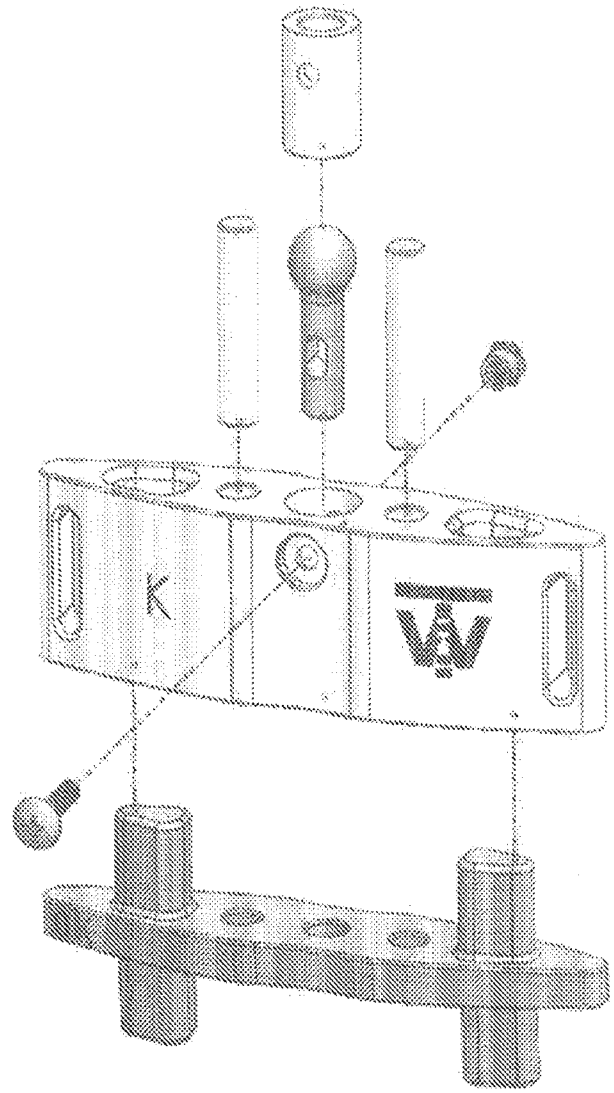
FIGS. 35-36 depict an embodiment of a portion of a spinal support system.
Figure 36:
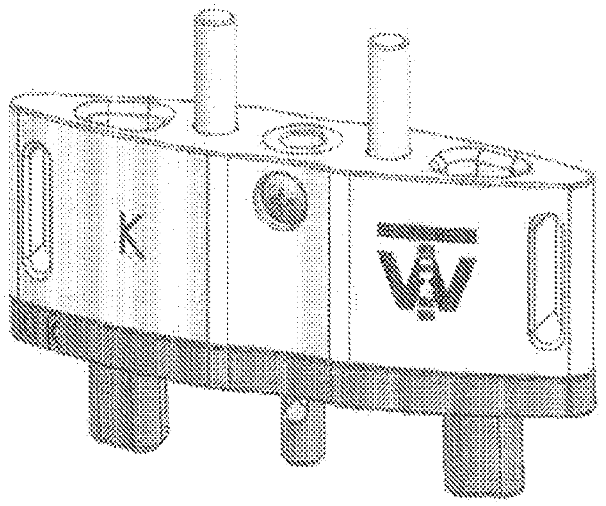

FIG. 33 illustrates how, in an embodiment, a plurality of rods is used to stabilize multiple segments. The rods are non-monolithic with rods separated from one another by, for example, space 3301. Such a space allows for compression/decompression within the brace and between the rods.

Rods may be somewhat flexible to allow limited movement of the brace. The rods may be formed from nylon, polyurethane, and the like.

Example 30b. The system according to any of examples 1b-29b, wherein: the first vertebral segment includes a maximum width; the first bushing includes a maximum width; the maximum width of the first vertebral segment is equal to the maximum width of the first bushing.

Figure 31C:
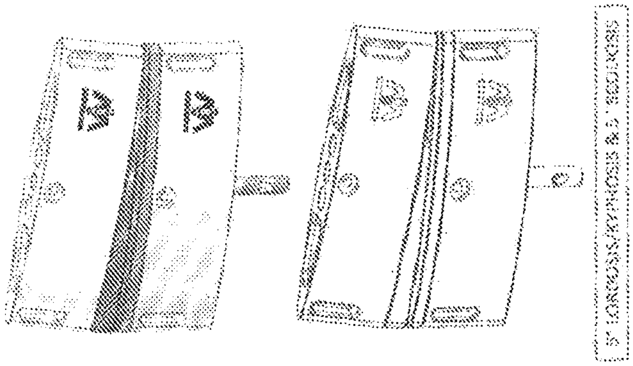
FIGS. 31A, 31B, 31C depict embodiments of subassemblies of modular wedge bushings.
Figure 31B:
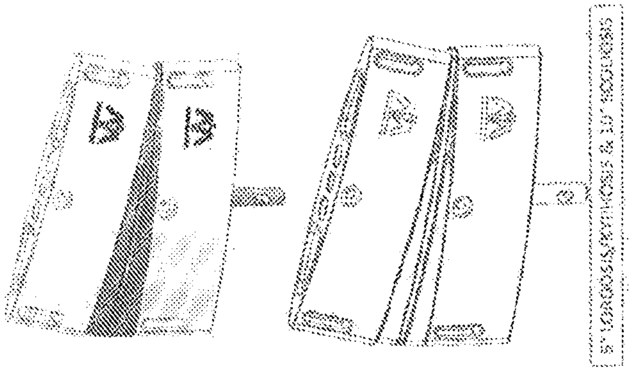
Figure 31A:
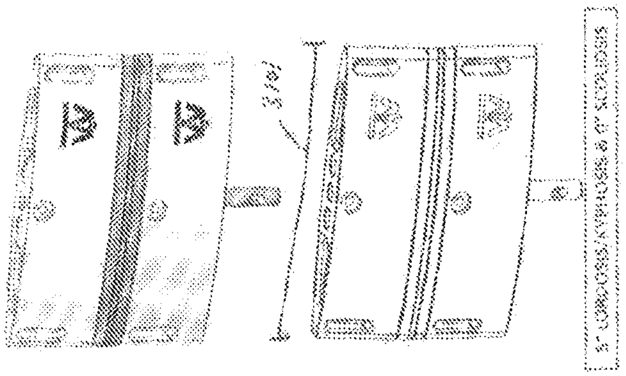

For example, see width 3101 of FIG. 31.

Example 31b. The system according to any of examples 1b-30b, wherein: the first vertebral segment includes a maximum width; the first bushing includes a maximum width; the maximum width of the first vertebral segment is unequal to the maximum width of the first bushing.

For example, see widths 3002, 3001 of FIG. 30. FIG. 30 discloses a bushing that is a wedge that is not as wide as the vertebral segment on which it lies.

Example 32b. The system according to example 31b comprising: a second bushing (234) between the first and second vertebral segments; wherein the second bushing includes a maximum width; the maximum width of the first bushing is unequal to the maximum width of the second bushing.

For example, in FIG. 30A a plurality of bushings of varying widths are used to obtain the desired level of scoliosis. Thus, more than one bushing may be included between vertebral segments. Further, while varying widths are addressed immediately above in other embodiments a plurality of bushings of varying dimensions (not limited to widths) are used to obtain the desired level of curvature.

Example 33b. The system according to any of examples 1b to 32b, wherein: a first portion of the first joint is included in the first vertebral segment; a second portion of the first joint is included in the second vertebral segment; a third portion of the first joint is included in the first bushing.

See, for example, FIG. 32(A).

Example 34b. The system according to any of examples 1b-33b, wherein the first joint is slidingly coupled to the first and second vertebral segments.

For example, FIG. 32(A) illustrates how joint 3201 includes aperture 3202 to receive anchor 3203. Aperture 3202 is wide enough to allow the joint to slide with respect to anchor 3203 to accommodate compression/decompression of the brace. See also void 3204 which also allows joint 3201 to slide. However, in other embodiments anchor 3203 does not slide. In other words, spaces 3202 and/or 3204 may cooperate to allow movement of elements with respect to each other, such as element 3201 with respect to element 3203. Joint 3201 may be considered, in an embodiment, to include a polyaxial post and vertebral segment in which is it received or, more generally, coupled.

Example 41b. An external spinal brace system comprising: a first vertebral segment (201); a first joint (204) that includes a first ball and socket joint; a second vertebral segment (202) to couple to the first vertebral segment via the first joint; a first bushing (231) to couple the first and second vertebral segments to one another in a first configuration; a second bushing to couple the first and second vertebral segments to one another in a second configuration. In the first configuration: (a) a sagittal plane intersects the first and second vertebral segments, the first and second joints, and the first bushing; (b) a coronal plane intersects one or more of: (b)(i) the first and second vertebral segments, (b)(ii) the first and second joints, and (b)(iii) the first bushing. Tn the second configuration: (a) a sagittal plane intersects the first and second vertebral segments, the first and second joints, and the first bushing; (b) a coronal plane intersects one or more of the first and second vertebral segments, the first and second joints, and the second bushing. The first bushing includes a superior surface disposed in a first plane of the first bushing and an inferior surface disposed in a second plane of the first bushing. The first and second planes of the first bushing intersect at a first angle of incidence. The second bushing includes a superior surface disposed in a first plane of the second bushing and an inferior surface disposed in a second plane of the second bushing. The first and second planes of the second bushing intersect at a second angle of incidence. The first and second angles of incidence are unequal to each other.

For example, in FIG. 25 the first bushing may include a 10-degree angle of incidence for scoliosis and the second bushing may include a 5-degree angle of incidence for scoliosis. The user may select which of the bushings to use in an interchangeable format to achieve a desired level of scoliosis. This kit of multiple bushings that are interchangeable with each other allows a user to customize the brace system according to the needs of the patient.

While in an embodiment, the first and second angles of incidence are unequal to each other, in another embodiment the first and second angles of incidence are equal to each other.

Example 42b. An external spinal brace system comprising: a first vertebral segment (201); a first joint (204) that includes a first ball and socket joint; a second vertebral segment (202) that couples to the first vertebral segment via the first joint; a second joint (205), which includes a second ball and socket joint, coupled to the second vertebral segment; and a first bushing (231) between the first and second vertebral segments. A sagittal plane (206) intersects the first and second vertebral segments, the first and second joints, and the first bushing. A coronal plane (207) intersects one or more of: (b)(i) the first and second vertebral segments, (b)(ii) the first and second joints, and (b)(iii) the first bushing. The first bushing includes first and second surfaces oriented to each other to provide a first degree of scoliotic curvature to the system.

Example 43b. The system according to example 42b comprising a second bushing that includes first and second surfaces oriented to each other to provide, when exchanged for the first bushing, a second degree of scoliotic curvature to the system. The first and second degrees of scoliotic curvature are unequal to each other.

Example 1d. An external spinal brace system comprising: a first vertebral segment (201); a first joint (204); a second vertebral segment (202) that couples to the first vertebral segment via the first joint; a second joint (205) coupled to the second vertebral segment; and a first modular spacer (231) between the first and second vertebral segments; wherein: (a) a sagittal plane (206) intersects the first and second vertebral segments, the first and second joints, and the first bushing; and (b) a coronal plane (207) intersects one or more of (b)(i) the first and second vertebral segments, (b)(ii) the first and second joints, (b)(iii) the first modular spacer, or (b)(iv) combinations thereof. The first modular spacer is non-rectilinear and includes a superior surface (232) that is not parallel to an inferior surface (233) of the first modular spacer.

Example 2d. The system according to example 1d, comprising: a third vertebral segment (243) that couples to the second vertebral segment via the second joint; and a second modular spacer (244) between the second and third vertebral segments. The second modular spacer is rectilinear and includes a superior surface (245) that is parallel to an inferior surface (246) of the second spacer.

Example 3d. The system according to example 1d, comprising: a third vertebral segment (243) that couples to the second vertebral segment via the second joint; a second modular spacer between the second and third vertebral segments. The second modular spacer is not rectilinear and includes a superior surface that is not parallel to an inferior surface of the second modular spacer.

The spacers are "modular" because they can be mixed and matched by a user to arrive at the proper forces to be applied to the patient.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An external spinal brace system comprising:
- a first vertebral segment including first and second voids;
- a first joint;
- a second vertebral segment that couples to the first vertebral segment via the first joint, the second vertebral segment including first and second voids;
- a second joint coupled to the second vertebral segment; and
- a first bushing between the first and second vertebral segments, the first bushing including first, second, third, and fourth projections;
- wherein: (a) a sagittal plane intersects the first and second vertebral segments, the first and second joints, and the first bushing; and (b) a coronal plane intersects one or more of (b)(i) the first and second vertebral segments, (b)(ii) the first and second joints, (b)(iii) the first bushing, or (b)(iv) combinations thereof;
- wherein: (a) the first bushing includes a superior surface disposed in a first plane of the first bushing and an inferior surface disposed in a second plane of the first bushing, and (b) the first plane of the first bushing is not parallel to the second plane of the first bushing;
- wherein the first projection is included in the first void of the first vertebral segment and the second projection is included in the second void of the first vertebral segment,
- wherein the third projection is included in the first void of the second vertebral segment and the fourth projection is included in the second void of the second vertebral segment.

2. The system according to claim 1, wherein the superior surface directly contacts the first vertebral segment.

3. The system according to claim 2, wherein the inferior surface directly contacts the second vertebral segment.

4. The system according to claim 1, comprising:
- a third vertebral segment that couples to the second vertebral segment via the second joint;
- a second bushing between the second and third vertebral segments;
- wherein: (a) the second bushing includes a superior surface disposed in a first plane of the second bushing and an inferior surface disposed in a second plane of the second bushing, and (b) the first plane of the second bushing is parallel to the second plane of the second bushing.

5. The system according to claim 1, comprising:
- a third vertebral segment that couples to the second vertebral segment via the second joint;
- a second bushing between the second and third vertebral segments;
- wherein: (a) the second bushing includes a superior surface disposed in a first plane of the second bushing and an inferior surface disposed in a second plane of the second bushing, and (b) the first plane of the second bushing is not parallel to the second plane of the second bushing.

6. The system according to claim 4, wherein the first plane of the first bushing is not parallel to the first plane of the second bushing.

7. The system according to claim 5, wherein:
- the first plane of the first bushing has a first degree of angle in the coronal plane;
- the first plane of the second bushing has a second degree of angle in the coronal plane;
- the first degree of angle in the coronal plane is unequal to the second degree of angle in the coronal plane.

8. The system according to claim 5, wherein:
- the first bushing is configured to impart a first degree of scoliosis;
- the second bushing is configured to impart a second degree of scoliosis;
- the first and second degrees of scoliosis are unequal to each other.

9. The system according to claim 5, wherein:
- the first plane of the first bushing has a first degree of angle in the sagittal plane;
- the first plane of the second bushing has a second degree of angle in the sagittal plane;
- the first degree of angle in the sagittal plane is unequal to the second degree of angle in the sagittal plane.

10. The system according to claim 5, wherein:
- the first bushing is configured to impart a first degree of lordosis;
- the second bushing is configured to impart a second degree of lordosis;
- the first degree of lordosis is unequal to the second degree of lordosis.

11. The system according to claim 5, wherein:
- the first bushing is configured to impart a first degree of kyphosis;
- the second bushing is configured to impart a second degree of kyphosis;
- the first degree of kyphosis is unequal to the second degree of kyphosis.

12. The system according to claim 5, wherein:
- the first bushing includes an aperture that couples the superior surface of the first bushing to the inferior surface of the first bushing;
- the aperture has a first maximum width where the aperture interfaces the superior surface of the first bushing;
- the aperture has a second maximum width where the aperture interfaces the inferior surface of the first bushing;
- the first maximum width is greater than the second maximum width.

13. The system according to claim 5 comprising a rod, wherein:
- the first vertebral segment includes an aperture having a first maximum width;

the second vertebral segment includes an aperture having a second maximum width that is unequal to the first maximum width of the aperture of the first vertebral segment;

the rod is included in the aperture of the first vertebral segment, the aperture of the second vertebral segment, and an aperture of the first bushing.

14. The system according to claim 1 comprising a sacral segment that couples to the second vertebral segment via the second joint;

wherein the sacral segment includes first and second ratchets, the first ratchet comprising a first toothed rack and a first spring-loaded finger and the second ratchet comprising a second toothed rack and a second spring-loaded finger;

wherein the first toothed rack includes a first outer surface that is curved in the sagittal plane and the second toothed rack includes a second outer surface that is curved in the sagittal plane.

15. The system of claim 14, wherein the first outer surface is rigid and non-malleable and the second outer surface is rigid and non-malleable.

16. The system of claim 15, wherein the first outer surface has a first center of curvature and at least a portion of the first toothed rack is between the first outer surface and the first center of curvature.

17. The system of claim 16 comprising a force sensor.

18. The system of claim 16, wherein the second joint is slidingly coupled to the sacral segment.

19. The system of claim 16, wherein the first toothed rack is slidingly coupled to the second toothed rack.

20. The system according to claim 5, wherein the system is configured to provide a torsional force to a patient's spine and a bending force to the patient's spine.

21. An external spinal brace system comprising:

a first vertebral segment;

a first joint;

a second vertebral segment that couples to the first vertebral segment via the first joint;

a second joint coupled to the second vertebral segment; and a first bushing between the first and second vertebral segments;

a sacral segment coupled to the second vertebral segment;

wherein: (a) a sagittal plane intersects the first and second vertebral segments, the first and second joints, and the first bushing; and (b) a coronal plane intersects one or more of (b)(i) the first and second vertebral segments, (b)(ii) the first and second joints, (b)(iii) the first bushing, or (b)(iv) combinations thereof;

wherein: (a) the first bushing includes a superior surface disposed in a first plane of the first bushing and an inferior surface disposed in a second plane of the first bushing, and (b) the first plane of the first bushing is not parallel to the second plane of the first bushing wherein the sacral segment includes a first body and a second body, the second body being slidably coupled to the first body;

wherein the first body includes a first outer surface that is curved in the sagittal plane and the second body includes a second outer surface that is curved in the sagittal plane.

22. The system of claim 21, wherein the first outer surface is rigid and non-malleable and the second outer surface is rigid and non-malleable.

23. The system of claim 21, comprising:

a third vertebral segment that couples to the second vertebral segment via the second joint;

a second bushing between the second and third vertebral segments;

wherein: (a) the second bushing includes a superior surface disposed in a first plane of the second bushing and an inferior surface disposed in a second plane of the second bushing, and (b) the first plane of the second bushing is parallel to the second plane of the second bushing.

24. The system of claim 21, comprising:

a third vertebral segment that couples to the second vertebral segment via the second joint;

a second bushing between the second and third vertebral segments;

wherein: (a) the second bushing includes a superior surface disposed in a first plane of the second bushing and an inferior surface disposed in a second plane of the second bushing, and (b) the first plane of the second bushing is not parallel to the second plane of the second bushing.

25. The system of claim 24, wherein:

the sacral segment includes at least one ratchet;

the at least one ratchet includes first and second ratchets, the first ratchet comprising a first toothed rack and a first spring-loaded finger and the second ratchet comprising a second toothed rack and a second spring-loaded finger;

wherein the first toothed rack includes the first outer surface that is curved in the sagittal plane and the second toothed rack includes the second outer surface that is curved in the sagittal plane.

26. The system of claim 25, wherein the first outer surface has a first center of curvature and at least a portion of the first toothed rack is between the first outer surface and the first center of curvature.

27. The system of claim 24, wherein:

the first plane of the first bushing has a first degree of angle in the coronal plane;

the first plane of the second bushing has a second degree of angle in the coronal plane;

the first degree of angle in the coronal plane is unequal to the second degree of angle in the coronal plane.

28. The system of claim 21 comprising a cord slidably coupled to at least one of the first or second bodies.

* * * * *